(12) United States Patent
Bogen et al.

(10) Patent No.: US 9,765,107 B2
(45) Date of Patent: Sep. 19, 2017

(54) CYCLIC PHOSPHONATE SUBSTITUTED NUCLEOSIDE DERIVATIVES AND METHODS OF USE THEREOF FOR THE TREATMENT OF VIRAL DISEASES

(71) Applicant: Merck Sharp & Dohme Corp., Rahway, NJ (US)

(72) Inventors: Stephane Bogen, Somerset, NJ (US); Vinay Girijavallabhan, Denville, NJ (US); Quang Truong, Morganville, NJ (US); Ping Chen, Edison, NJ (US); Frank Bennett, Cranford, NJ (US); Angela Kerekes, Plainfield, NJ (US); Qun Dang, Westfield, NJ (US); David B. Olsen, Lansdale, PA (US); Ian Davies, Princeton, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 14/899,008

(22) PCT Filed: Jun. 16, 2014

(86) PCT No.: PCT/US2014/042463
§ 371 (c)(1),
(2) Date: Dec. 16, 2015

(87) PCT Pub. No.: WO2014/204831
PCT Pub. Date: Dec. 24, 2014

(65) Prior Publication Data
US 2016/0122380 A1 May 5, 2016

Related U.S. Application Data

(60) Provisional application No. 61/836,342, filed on Jun. 18, 2013.

(51) Int. Cl.

| | | |
|---|---|---|
| *A01N 43/04* | (2006.01) | |
| *A61K 31/70* | (2006.01) | |
| *C07H 19/10* | (2006.01) | |
| *A61K 45/06* | (2006.01) | |
| *A61K 31/661* | (2006.01) | |
| *C07F 9/6558* | (2006.01) | |
| *C07F 9/6574* | (2006.01) | |
| *C07H 19/11* | (2006.01) | |
| *A61K 31/7072* | (2006.01) | |
| *A61K 31/7068* | (2006.01) | |
| *A61K 31/706* | (2006.01) | |
| *A61K 31/7064* | (2006.01) | |

(52) U.S. Cl.
CPC ........... *C07H 19/10* (2013.01); *A61K 31/661* (2013.01); *A61K 31/7072* (2013.01); *A61K 45/06* (2013.01); *C07F 9/65586* (2013.01); *C07F 9/65744* (2013.01); *C07H 19/11* (2013.01); *A61K 31/706* (2013.01); *A61K 31/7064* (2013.01); *A61K 31/7068* (2013.01)

(58) Field of Classification Search
None
See application file for complete search history.

(56) References Cited

U.S. PATENT DOCUMENTS

| | | | |
|---|---|---|---|
| 7,879,815 | B2 | 2/2011 | MacCoss et al. |
| 2009/0081636 | A1 | 3/2009 | Huang |
| 2012/0258928 | A1 | 10/2012 | Du et al. |

FOREIGN PATENT DOCUMENTS

| | | |
|---|---|---|
| WO | 2005003147 | 1/2005 |
| WO | 2008082464 | 7/2008 |
| WO | 2008082488 | 7/2008 |
| WO | 2008082602 | 7/2008 |
| WO | 2008083351 | 7/2008 |
| WO | 2008136815 | 11/2008 |
| WO | 2009032116 | 3/2009 |
| WO | 2009032123 | 3/2009 |
| WO | 2009032124 | 3/2009 |
| WO | 2009032125 | 3/2009 |
| WO | 2009132123 A1 | 10/2009 |
| WO | 2010002877 | 1/2010 |
| WO | 2010075517 | 7/2010 |
| WO | 2010075549 | 7/2010 |

(Continued)

OTHER PUBLICATIONS

Chamberlin et al. PNAS (2002), vol. 99, pp. 14688-14693.*

(Continued)

*Primary Examiner* — Patrick Lewis
(74) *Attorney, Agent, or Firm* — Jeffrey P. Bergman; Catherine D. Fitch

(57) ABSTRACT

The present invention relates to Cyclic Phosphonate Substituted Nucleoside Derivatives of Formula (I): (structure) and pharmaceutically acceptable salts thereof, wherein B, X, R1, R2 and R3 are as defined herein, as well as to compositions and methods of using the Cyclic Phosphonate Substituted Nucleoside Derivatives for treating or preventing HCV infection in a patient.

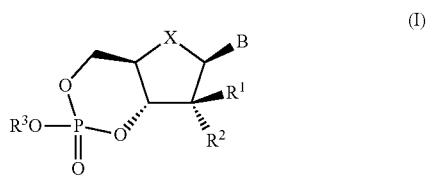

(I)

13 Claims, No Drawings

(56) References Cited

FOREIGN PATENT DOCUMENTS

| WO | 2011003521 A1 | 1/2011 |
| WO | 2011035231 | 3/2011 |
| WO | 2012142085 A1 | 10/2012 |

OTHER PUBLICATIONS

Asselah et al., Protease and polymerase inhibitors for the treatmentof hepatitis C, Liver International, 2009, 57-67, 29(s1).
Balsano, Recent Advances in Antiviral Agents: Established and Innovative Therapies for Viral Hepatitis, Mini-Reviews in Medicinal Chemistry, 2008, pp. 307-318, 8(4).
Beaulieu et al., Inhibitors of the HCV NS5B polymerase: New hope for the treatment of hepatitis C infections, Current Opinions in Investigational Drugs, 2004, 838, 5.
Berge et al., Pharmaceutical Salts, J. Pharm Sci., 1977, pp. 1-19, 66(1).
Bingham et al., Over one hundred solvates of sulfathiazole, Chem. Commun., 2001, 603-604.
Bobeck et al., Advances in nucleoside monophosphate prodrugs as anti-HCV agents, Antiviral Therapy, 2010, 935-950, 15.
Caira et al., Preparation and Crystal Characterization of a Polymorph,a Monohydrate, and an Ethyl Acetate Solvate of the Antifungal Fluconazole, J, Pharmaceutical Sci, 2004, 601-611, 93(3).
Dore et al., The changing therapeutic landscape for hepatitis C, Med. J. Australia, 2012, 629-632, 196.
Eldrup et al., Structure-Activity Relationship of Purine Ribonucleosides for Inhibition of Hepatitis C Virus RNA-Dependent RNA Polymerase, J. Med. Chem., 2004, 2283-2295, 47.
Erion, "Microsomes and Drug Oxidations", Proceedings of the International Symposium, 17th, 2008, pp. 7-12, saratoga Sprints, NY, US.
Furman et al., Nucleoside analog inhibitors of hepatitis C viral replication: recent advances, challenges and trends, Future Medicinal Chemistry, 2009, 1429-1452, 1.
Gould, Salt selection for basic drugs, International J. of Pharmaceutics, 1986, 201-217, 33.
Green & Wuts, Protective Groups in Organic Synthesis, 2nd Edition, 1991, –, –.
Holland et al., Hepatitis C genotyping by direct sequencing of the product from the Roche amplicor test: Methodology and application to a South Australian population, Pathology, 1998, 192-195, 30.
Ishii et al., Expression of Hepatitis C Virus NS5B Protein: Characterization of Its RNA Polymerase Activity and RNA Binding, Hepatology, 1999, 1227-1235, 29.
Lohmann et al., Biochemical and Kinetic Analyses of NS5B RNA-Dependent RNA Polymerase of the Hepatitis C Virus, Virology, 1998, 108-118, 249.
Ni et al., Progress and Development of Small Molecule HCV Antivirals, Current Opinion in Drug Discovery and Development, 2004, 446, 7(4).
Poordad et al., Treating hepatitis C: current standard of care and emerging direct-acting antiviral agents, Journal of Viral Hepatitis, 2012, 449-464, 19.
Simmonds et al., Classification of hepatitis C virus into six major genotypes and a series of, J. Gen Virol, 1993, 2391-2399, 74(Pt11).
T. Higuchi and V. Stella, Pro-drugs as NovelDelivery Systems (1987) 14 of the A.C.S. Symposium Series.
Tan et al., Hepatitis C Therapeutics: Current Status and Emerging Strategies, Nature Reviews, 2002, 867-881, 1.
Van Tonder, et al, Preparation and Physicochemical Characterization of 5 Niclosamide Solvates and 1 Hemisolvate, AAPS PharmsciTech, 2004, pp. 1-10, 5(1), US.
Y. Mehellou, "Phosphoramidate Prodrugs Deliver with Potency Against Hepatitis C Virus", Chem. Med. Chem., 2010, pp. 1841-1842, vol. 5.

* cited by examiner

CYCLIC PHOSPHONATE SUBSTITUTED NUCLEOSIDE DERIVATIVES AND METHODS OF USE THEREOF FOR THE TREATMENT OF VIRAL DISEASES

CROSS-REFERENCE TO RELATED APPLICATIONS

This application is the national stage application under 35 U.S.C. 371 of International Patent Application No. PCT/US14/042463, filed Jun. 16, 2014, which claims priority to U.S. Provisional Patent Application No. 61/836,342, filed Jun. 18, 2013. Each of the aforementioned applications is incorporated by reference in its entirety.

FIELD OF THE INVENTION

The present invention relates to Cyclic Phosphonate Substituted Nucleoside Derivatives, compositions comprising at least one Cyclic Phosphonate Substituted Nucleoside Derivative, and methods of using the Cyclic Phosphonate Substituted Nucleoside Derivatives for treating or preventing HCV infection in a patient.

BACKGROUND OF THE INVENTION

Hepatitis C virus (HCV) infection is a major health problem that leads to chronic liver disease, such as cirrhosis and hepatocellular carcinoma, in a substantial number of infected individuals, estimated to be 2-15% of the world's population. There are over 3 million chronically infected people in the United States alone, according to the U.S. Center for Disease Control. About 150 million individuals are chronically infected worldwide, with at least 3 to 4 million people being infected each year. Hepatitis C Fact Sheet, World Health Organization, July 2012. Once infected, about 20% of people clear the virus, but the rest harbor HCV the rest of their lives. Ten to twenty percent of chronically infected individuals eventually develop liver-destroying cirrhosis or cancer. HCV is transmitted parenterally by contaminated blood and blood products, contaminated needles, or sexually and vertically from infected mothers or carrier mothers to their off-spring.

Different approaches to HCV therapy have been taken, which include the inhibition of viral serine proteinase (NS3 protease), helicase, and RNA-dependent RNA polymerase (NS5B), and the development of a vaccine. Current and investigational treatments for HCV infection are reviewed in Poordad et al., Treating hepatitis C: current standard of care and emerging direct-acting antiviral agents. *Journal of Viral Hepatitis* 19: 449-464 (2012); Asselah et al., Protease and polymerase inhibitors for the treatment of hepatitis C. *Liver International* 29(s1): 57-67 (2009); G. J. Dore. The changing therapeutic landscape for hepatitis C. *Med. J. Australia* 196: 629-632 (2012); and Balsano, *Mini Rev. Med. Chem.* 8(4): 307-318, 2008. Despite the availability of therapeutic treatment options, chronic HCV infection remains a major healthcare concern. Moreover, there is no established vaccine for HCV. Consequently, there is a need for improved therapeutic agents that effectively combat chronic HCV infection.

The HCV virion is an enveloped positive-strand RNA virus with a single oligoribonucleotide genomic sequence of about 9400 bases which encodes a polyprotein of about 3,000 amino acids. The protein products of the HCV gene consist of the structural proteins C, E1, and E2, and the non-structural proteins NS2, NS3, NS4A, NS4B, NS5A and NS5B. The nonstructural (NS) proteins are believed to provide the catalytic machinery for viral replication.

The NS3 protease releases NS5B, the RNA-dependent RNA polymerase from the polyprotein chain. HCV NS5B polymerase is required for the synthesis of a negative-strand RNA intermediate from a positive-strand genomic viral RNA that serves as a template in the replication cycle of HCV. NS5B polymerase is an essential component in the HCV replication complex. See K. Ishi, et al., "Expression of Hepatitis C Virus NS5B Protein: Characterization of Its RNA Polymerase Activity and RNA Binding," *Hepatology*, 29:1227-1235 (1999) and V. Lohmann, et al., "Biochemical and Kinetic Analyses of NS5B RNA-Dependent RNA Polymerase of the Hepatitis C Virus," Virology, 249: 108-118 (1998) Inhibition of HCV NS5B polymerase prevents formation of the double-stranded HCV RNA and therefore constitutes an attractive approach to the development of HCV-specific antiviral therapies.

The development of inhibitors of HCV NS5B polymerase with potential for the treatment of HCV infection has been reviewed in Poordad et al. (2012), supra; Asselah et al. (2009), supra; and Chatel-Chaix et al. Direct-acting and host-targeting HCV inhibitors: current and future directions. *Current Opinion in Virology*, 2:588-598 (2012). The activity of purine ribonucleosides against HCV polymerase was reported by A. E. Eldrup et al., "Structure-Activity Relationship of Purine Ribonucleosides for Inhibition of HCV RNA-Dependent RNA Polymerase," *J. Med. Chem.*, 47:2283-2295 (2004). Nucleoside analogs said to be useful in the treatment of hepatitis C are disclosed in WO 2011/035231, WO 2005/003147, WO 2010/0081628, U.S. Pat. No. 7,879,815, WO 2010/075517, WO 2010/002877, and WO 2009/132123.

SUMMARY OF THE INVENTION

In one aspect, the present invention provides Compounds of Formula (I):

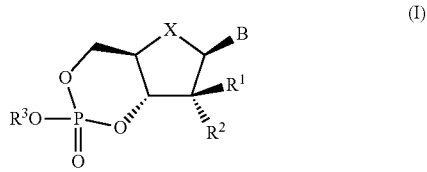

or a pharmaceutically acceptable salt thereof, wherein:

B is:

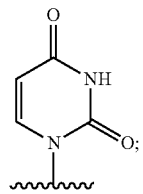

X is O, N, S or $CH_2$;
$R^1$ is H, $C_1$-$C_3$ alkyl, $C_2$-$C_3$ alkenyl or $C_2$-$C_3$ alkynyl;
$R^2$ is —$N(R^6)_2$;
$R^3$ is H, $C_6$-$C_{20}$ alkyl, —($C_1$-$C_3$ alkylene)$_m$-($C_3$-$C_7$ cycloalkyl) or —($C_1$-$C_3$ alkylene)$_m$-($C_6$-$C_{10}$ aryl); wherein said $C_6$-$C_{20}$ alkyl group, said $C_3$-$C_7$ cycloalkyl group and said $C_6$-$C_{10}$ aryl group can be optionally substituted with up to five groups, each independently selected from $C_1$-$C_6$ alkyl, $C_2$-$C_6$ alkenyl, $C_2$-$C_6$ alkynyl, $C_3$-$C_7$ cycloalkyl, $C_6$-$C_{10}$ aryl, 5- or 6-membered monocyclic heteroaryl, 9- or 10-membered bicyclic heteroaryl, halo, —$OR^7$, —$SR^7$, —$S(O)R^7$, —$S(O)_2R^7$, —$S(O)_2N(R^7)_2$, $C_1$-$C_6$ haloalkyl, $C_1$-$C_6$ hydroxyalkyl, —O—($C_1$-$C_6$ haloalkyl), —CN, —$NO_2$, —$N(R^7)_2$, —$C(O)OR^7$, —$C(O)N(R^7)_2$ and —NHC$(O)R^7$, —NHC(O)$OR^7$ and —NHC(O)N$(R^7)_2$;

each occurrence of $R^4$ is independently H, $C_1$-$C_6$ alkyl, $C_1$-$C_6$ haloalkyl, $C_1$-$C_6$ hydroxyalkyl, —($C_1$-$C_3$ alkylene)$_m$-($C_3$-$C_7$ cycloalkyl), —($C_1$-$C_3$ alkylene)$_m$-($C_6$-$C_{10}$ aryl), —($C_1$-$C_3$ alkylene)$_m$-(4 to 7-membered heterocycloalkyl), —($C_1$-$C_3$ alkylene)$_m$-(5- or 6-membered monocyclic heteroaryl) or —($C_1$-$C_3$ alkylene)$_m$-(9- or 10-membered bicyclic heteroaryl);

$R^5$ is H or —C(O)—($C_1$-$C_{20}$ alkyl);

each occurrence of $R^6$ is independently H, $C_1$-$C_6$ alkyl, $C_3$-$C_7$ cycloalkyl, phenyl or benzyl;

each occurrence of $R^7$ is independently H, $C_1$-$C_{10}$ alkyl, $C_1$-$C_6$ haloalkyl, $C_1$-$C_6$ hydroxyalkyl, —($C_1$-$C_3$ alkylene)$_m$-($C_3$-$C_7$ cyclo alkyl), —($C_1$-$C_3$ alkylene)$_m$-($C_6$-$C_{10}$ aryl), —($C_1$-$C_3$ alkylene)$_m$-(4 to 7-membered heterocycloalkyl), —($C_1$-$C_3$ alkylene)$_m$-(5- or 6-membered monocyclic heteroaryl) or —($C_1$-$C_3$ alkylene)$_m$-(9- or 10-membered bicyclic heteroaryl), wherein said $C_3$-$C_7$ cycloalkyl group, said $C_6$-$C_{10}$ aryl group, said 4 to 7-membered heterocycloalkyl group, said -5- or 6-membered monocyclic heteroaryl group or said 9- or 10-membered bicyclic heteroaryl group can be optionally substituted with $R^8$;

$R^8$ represents from one to five substituent groups, each independently selected from $C_1$-$C_6$ alkyl, $C_2$-$C_6$ alkenyl, $C_2$-$C_6$ alkynyl, halo, —$OR^4$, —$SR^4$, $C_1$-$C_6$ haloalkyl, $C_1$-$C_6$ hydroxyalkyl, —O—($C_1$-$C_6$ haloalkyl), —CN, —$NO_2$, —$N(R^4)_2$, —$C(O)OR^4$, —$C(O)N(R^4)_2$ and —NHC(O)$R^4$; and each occurrence of m is independently 0 or 1.

The Compounds of Formula (I) (also referred to herein as the "Cyclic Phosphonate Substituted Nucleoside Derivatives") and pharmaceutically acceptable salts thereof can be useful, for example, for inhibiting HCV viral replication or replicon activity, for inhibiting HCV NS5B activity, and for treating or preventing HCV infection in a patient. Without being bound by any specific theory, it is believed that the Cyclic Phosphonate Substituted Nucleoside Derivatives inhibit HCV viral replication by inhibiting HCV NS5B.

Accordingly, the present invention provides methods for treating or preventing HCV infection in a patient, comprising administering to the patient an effective amount of at least one Cyclic Phosphonate Substituted Nucleoside Derivative.

The details of the invention are set forth in the accompanying detailed description set forth below.

Other embodiments, aspects and features of the present invention are either further described in or will be apparent from the ensuing description, examples and appended claims.

DETAILED DESCRIPTION OF THE INVENTION

The present invention relates to Cyclic Phosphonate Substituted Nucleoside Derivatives, compositions comprising at least one Cyclic Phosphonate Substituted Nucleoside Derivative, and methods of using the Cyclic Phosphonate Substituted Nucleoside Derivatives for treating or preventing HCV infection in a patient.

Definitions and Abbreviations

The terms used herein have their ordinary meaning and the meaning of such terms is independent at each occurrence thereof. That notwithstanding and except where stated otherwise, the following definitions apply throughout the specification and claims. Chemical names, common names, and chemical structures may be used interchangeably to describe the same structure. If a chemical compound is referred to using both a chemical structure and a chemical name and an ambiguity exists between the structure and the name, the structure predominates. These definitions apply regardless of whether a term is used by itself or in combination with other terms, unless otherwise indicated. Hence, the definition of "alkyl" applies to "alkyl" as well as the "alkyl" portions of "hydroxyalkyl," "haloalkyl," "—O-alkyl," etc. . . .

As used herein, and throughout this disclosure, the following terms, unless otherwise indicated, shall be understood to have the following meanings:

A "patient" is a human or non-human mammal. In one embodiment, a patient is a human. In another embodiment, a patient is a chimpanzee.

The term "effective amount" as used herein, refers to an amount of Cyclic Phosphonate Substituted Nucleoside Derivative and/or an additional therapeutic agent, or a composition thereof that is effective in producing the desired therapeutic, ameliorative, inhibitory or preventative effect when administered to a patient suffering from a viral infection or virus-related disorder. In the combination therapies of the present invention, an effective amount can refer to each individual agent or to the combination as a whole, wherein the amounts of all agents administered are together effective, but wherein the component agent of the combination may not be present individually in an effective amount.

The term "preventing," as used herein with respect to an HCV viral infection or HCV-virus related disorder, refers to reducing the likelihood or severity of HCV infection.

The term "alkyl," as used herein, refers to an aliphatic hydrocarbon group having one of its hydrogen atoms replaced with a bond. An alkyl group may be straight or branched and contain from about 1 to about 20 carbon atoms. In one embodiment, an alkyl group contains from about 1 to about 12 carbon atoms. In different embodiments, an alkyl group contains from 1 to 6 carbon atoms ($C_1$-$C_6$ alkyl) or from about 1 to about 4 carbon atoms ($C_1$-$C_4$ alkyl). Non-limiting examples of alkyl groups include methyl, ethyl, n-propyl, isopropyl, n-butyl, sec-butyl, isobutyl, tert-butyl, n-pentyl, neopentyl, isopentyl, n-hexyl, isohexyl and neohexyl. An alkyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —$NH_2$, —NH(alkyl), —N(alkyl)$_2$, —NH(cycloalkyl), —O—C(O)-alkyl, —O—C(O)-aryl, —O—C(O)-cycloalkyl, —C(O)OH and —C(O)O-alkyl. In one embodiment, an alkyl group is linear. In another embodiment, an alkyl group is branched. Unless otherwise indicated, an alkyl group is unsubstituted.

The term "alkenyl," as used herein, refers to an aliphatic hydrocarbon group containing at least one carbon-carbon double bond and having one of its hydrogen atoms replaced with a bond. An alkenyl group may be straight or branched and contain from about 2 to about 15 carbon atoms. In one embodiment, an alkenyl group contains from about 2 to about 12 carbon atoms. In another embodiment, an alkenyl group contains from about 2 to about 6 carbon atoms. Non-limiting examples of alkenyl groups include ethenyl, propenyl, n-butenyl, 3-methylbut-2-enyl, n-pentenyl, octenyl and decenyl. An alkenyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —NH$_2$, —NH(alkyl), —N(alkyl)$_2$, —NH(cycloalkyl), —O—C(O)-alkyl, —O—C(O)-aryl, —O—C(O)-cycloalkyl, —C(O)OH and —C(O)O-alkyl. The term "C$_2$-C$_6$ alkenyl" refers to an alkenyl group having from 2 to 6 carbon atoms. Unless otherwise indicated, an alkenyl group is unsubstituted.

The term "alkynyl," as used herein, refers to an aliphatic hydrocarbon group containing at least one carbon-carbon triple bond and having one of its hydrogen atoms replaced with a bond. An alkynyl group may be straight or branched and contain from about 2 to about 15 carbon atoms. In one embodiment, an alkynyl group contains from about 2 to about 12 carbon atoms. In another embodiment, an alkynyl group contains from about 2 to about 6 carbon atoms. Non-limiting examples of alkynyl groups include ethynyl, propynyl, 2-butyryl and 3-methylbutynyl. An alkynyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —NH$_2$, —NH(alkyl), —N(alkyl)$_2$, —NH(cycloalkyl), —O—C(O)-alkyl, —O—C(O)-aryl, —O—C(O)-cycloalkyl, —C(O)OH and —C(O)O-alkyl. The term "C$_2$-C$_6$ alkynyl" refers to an alkynyl group having from 2 to 6 carbon atoms. Unless otherwise indicated, an alkynyl group is unsubstituted.

The term "alkylene," as used herein, refers to an alkyl group, as defined above, wherein one of the alkyl group's hydrogen atoms has been replaced with a bond. Non-limiting examples of alkylene groups include —CH$_2$—, —CH$_2$CH$_2$—, —CH$_2$CH$_2$CH$_2$—, —CH$_2$CH$_2$CH$_2$CH$_2$—, —CH(CH$_3$)CH$_2$CH$_2$—, —CH(CH$_3$)— and —CH$_2$CH(CH$_3$)CH$_2$—. In one embodiment, an alkylene group has from 1 to about 6 carbon atoms. In another embodiment, an alkylene group is branched. In another embodiment, an alkylene group is linear. In one embodiment, an alkylene group is —CH$_2$—. The term "C$_1$-C$_6$ alkylene" refers to an alkylene group having from 1 to 6 carbon atoms.

The term "aryl," as used herein, refers to an aromatic monocyclic or multicyclic ring system comprising from about 6 to about 14 carbon atoms. In one embodiment, an aryl group contains from about 6 to about 10 carbon atoms. An aryl group can be optionally substituted with one or more "ring system substituents" which may be the same or different, and are as defined herein below. In one embodiment, an aryl group can be optionally fused to a cycloalkyl or cycloalkanoyl group. Non-limiting examples of aryl groups include phenyl and naphthyl. In one embodiment, an aryl group is phenyl. Unless otherwise indicated, an aryl group is unsubstituted.

The term "arylene," as used herein, refers to a bivalent group derived from an aryl group, as defined above, by removal of a hydrogen atom from a ring carbon of an aryl group. An arylene group can be derived from a monocyclic or multicyclic ring system comprising from about 6 to about 14 carbon atoms. In one embodiment, an arylene group contains from about 6 to about 10 carbon atoms. In another embodiment, an arylene group is a naphthylene group. In another embodiment, an arylene group is a phenylene group. An arylene group can be optionally substituted with one or more "ring system substituents" which may be the same or different, and are as defined herein below. An arylene group is divalent and either available bond on an arylene group can connect to either group flanking the arylene group. For example, the group "A-arylene-B," wherein the arylene group is:

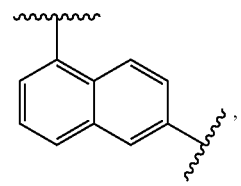 [SMILES: *c1ccc2c(*)cccc2c1]

is understood to represent both:

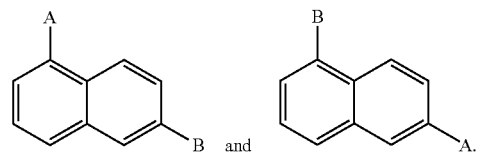

In one embodiment, an arylene group can be optionally fused to a cycloalkyl or cycloalkanoyl group. Non-limiting examples of arylene groups include phenylene and naphthalene. In one embodiment, an arylene group is unsubstituted. In another embodiment, an arylene group is:

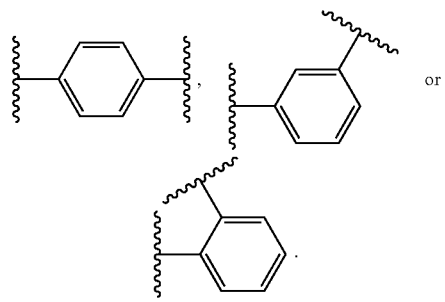

Unless otherwise indicated, an arylene group is unsubstituted.

The term "cycloalkyl," as used herein, refers to a non-aromatic mono- or multicyclic ring system comprising from 3 to about 10 ring carbon atoms. In one embodiment, a cycloalkyl contains from about 5 to about 10 ring carbon atoms. In another embodiment, a cycloalkyl contains from 3 to about 7 ring atoms. In another embodiment, a cycloalkyl contains from about 5 to about 6 ring atoms. The term "cycloalkyl" also encompasses a cycloalkyl group, as defined above, which is fused to an aryl (e.g., benzene) or heteroaryl ring. Non-limiting examples of monocyclic cycloalkyls include cyclopropyl, cyclobutyl, cyclopentyl, cyclohexyl, cycloheptyl and cyclooctyl. Non-limiting examples of multicyclic cycloalkyls include 1-decalinyl, norbornyl and adamantyl. A cycloalkyl group can be optionally substituted with one or more "ring system substituents" which may be the same or different, and are as defined herein below. In one embodiment, a cycloalkyl group is unsubstituted. The term "3 to 6-membered cycloalkyl" refers to a cycloalkyl group having from 3 to 6 ring carbon atoms. Unless otherwise indicated, a cycloalkyl group is unsubstituted. A ring carbon atom of a cycloalkyl group may be functionalized as a carbonyl group. An illustrative example of such a cycloalkyl group (also referred to herein as a "cycloalkanoyl" group) includes, but is not limited to, cyclobutanoyl:

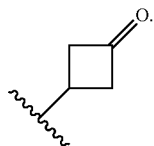 [SMILES: *C1CC(=O)C1]

The term "halo," as used herein, means —F, —Cl, —Br or —I.

The term "haloalkyl," as used herein, refers to an alkyl group as defined above, wherein one or more of the alkyl group's hydrogen atoms have been replaced with a halogen. In one embodiment, a haloalkyl group has from 1 to 6 carbon atoms. In another embodiment, a haloalkyl group is substituted with from 1 to 3 F atoms. Non-limiting examples of haloalkyl groups include —CH$_2$F, —CHF$_2$, —CF$_3$, —CH$_2$Cl and —CCl$_3$. The term "C$_1$-C$_6$ haloalkyl" refers to a haloalkyl group having from 1 to 6 carbon atoms.

The term "hydroxyalkyl," as used herein, refers to an alkyl group as defined above, wherein one or more of the alkyl group's hydrogen atoms have been replaced with an —OH group. In one embodiment, a hydroxyalkyl group has from 1 to 6 carbon atoms. Non-limiting examples of hydroxyalkyl groups include —CH$_2$OH, —CH$_2$CH$_2$OH, —CH$_2$CH$_2$CH$_2$OH and —CH$_2$CH(OH)CH$_3$. The term "C$_1$-C$_6$ hydroxyalkyl" refers to a hydroxyalkyl group having from 1 to 6 carbon atoms.

The term "heteroaryl," as used herein, refers to an aromatic monocyclic or multicyclic ring system comprising about 5 to about 14 ring atoms, wherein from 1 to 4 of the ring atoms is independently O, N or S and the remaining ring atoms are carbon atoms. In one embodiment, a heteroaryl group has 5 to 10 ring atoms. In another embodiment, a heteroaryl group is monocyclic and has 5 or 6 ring atoms. In another embodiment, a heteroaryl group is bicyclic. A heteroaryl group can be optionally substituted by one or more "ring system substituents" which may be the same or different, and are as defined herein below. A heteroaryl group is joined via a ring carbon atom, and any nitrogen atom of a heteroaryl can be optionally oxidized to the corresponding N-oxide. The term "heteroaryl" also encompasses a heteroaryl group, as defined above, which is fused to a benzene ring. Non-limiting examples of heteroaryls include pyridyl, pyrazinyl, furanyl, thienyl, pyrimidinyl, pyridone (including N-substituted pyridones), isoxazolyl, isothiazolyl, oxazolyl, oxadiazolyl, thiazolyl, pyrazolyl, furazanyl, pyrrolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, benzimidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like, and all isomeric forms thereof. The term "heteroaryl" also refers to partially saturated heteroaryl moieties such as, for example, tetrahydroisoquinolyl, tetrahydroquinolyl and the like. In one embodiment, a heteroaryl group is a 5-membered heteroaryl. In another embodiment, a heteroaryl group is a 6-membered heteroaryl. In another embodiment, a heteroaryl group comprises a 5- to 6-membered heteroaryl group fused to a benzene ring. Unless otherwise indicated, a heteroaryl group is unsubstituted.

The term "heterocycloalkyl," as used herein, refers to a non-aromatic saturated monocyclic or multicyclic ring system comprising 3 to about 11 ring atoms, wherein from 1 to 4 of the ring atoms are independently O, S, N or Si, and the remainder of the ring atoms are carbon atoms. A heterocycloalkyl group can be joined via a ring carbon, ring silicon atom or ring nitrogen atom. In one embodiment, a heterocycloalkyl group is monocyclic and has from 3 to about 7 ring atoms. In another embodiment, a heterocycloalkyl group is monocyclic has from about 4 to about 7 ring atoms. In another embodiment, a heterocycloalkyl group is bicyclic and has from about 7 to about 11 ring atoms. In still another embodiment, a heterocycloalkyl group is monocyclic and has 5 or 6 ring atoms. In one embodiment, a heterocycloalkyl group is monocyclic. In another embodiment, a heterocycloalkyl group is bicyclic. There are no adjacent oxygen and/or sulfur atoms present in the ring system. Any —NH group in a heterocycloalkyl ring may exist protected such as, for example, as an —N(BOC), —N(Cbz), —N(Tos) group and the like; such protected heterocycloalkyl groups are considered part of this invention. The term "heterocycloalkyl" also encompasses a heterocycloalkyl group, as defined above, which is fused to an aryl (e.g., benzene) or heteroaryl ring. A heterocycloalkyl group can be optionally substituted by one or more "ring system substituents" which may be the same or different, and are as defined herein below. The nitrogen or sulfur atom of the heterocycloalkyl can be optionally oxidized to the corresponding N-oxide, S-oxide or S,S-dioxide. Non-limiting examples of monocyclic heterocycloalkyl rings include oxetanyl, piperidyl, pyrrolidinyl, piperazinyl, morpholinyl, thiomorpholinyl, thiazolidinyl, 1,4-dioxanyl, tetrahydrofuranyl, tetrahydrothiophenyl, delta-lactam, delta-lactone, silacyclopentane, silapyrrolidine and the like, and all isomers thereof. Non-limiting illustrative examples of a silyl-containing heterocycloalkyl group include:

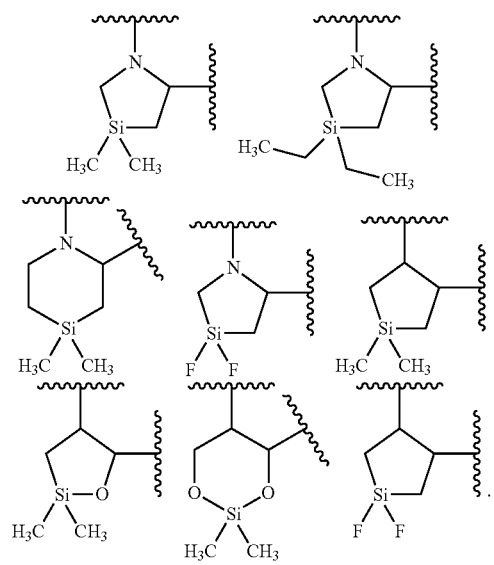

A ring carbon atom of a heterocycloalkyl group may be functionalized as a carbonyl group. An illustrative example of such a heterocycloalkyl group is:

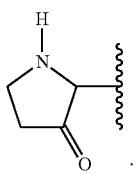 [SMILES: *C1NCCC1=O]

In one embodiment, a heterocycloalkyl group is a 5-membered monocyclic heterocycloalkyl. In another embodiment, a heterocycloalkyl group is a 6-membered monocyclic heterocycloalkyl. The term "3 to 6-membered monocyclic cycloalkyl" refers to a monocyclic heterocycloalkyl group having from 3 to 6 ring atoms. The term "4 to 6-membered monocyclic cycloalkyl" refers to a monocyclic heterocycloalkyl group having from 4 to 6 ring atoms. The term "7 to 11-membered bicyclic heterocycloalkyl" refers to a bicyclic heterocycloalkyl group having from 7 to 11 ring atoms. Unless otherwise indicated, an heterocycloalkyl group is unsubstituted.

The term "ring system substituent," as used herein, refers to a substituent group attached to an aromatic or non-aromatic ring system which, for example, replaces an available hydrogen on the ring system. Ring system substituents may be the same or different. Illustrative example of ring system substituents include, but are not limited to, alkyl, alkenyl, alkynyl, aryl, heteroaryl, -alkylene-aryl, -arylene-alkyl, -alkylene-heteroaryl, -alkenylene-heteroaryl, -alkynylene-heteroaryl, —OH, hydroxyalkyl, haloalkyl, —O-alkyl, —O-haloalkyl, -alkylene-O-alkyl, —O-aryl, —O-alkylene-aryl, acyl, —C(O)-aryl, halo, —NO$_2$, —CN, —SF$_5$, —C(O)OH, —C(O)O-alkyl, —C(O)O-aryl, —C(O)O-alkylene-aryl, —S(O)-alkyl, —S(O)$_2$-alkyl, —S(O)-aryl, —S(O)$_2$-aryl, —S(O)-heteroaryl, —S(O)$_2$-heteroaryl, —S-alkyl, —S-aryl, —S-heteroaryl, —S-alkylene-aryl, —S-alkylene-heteroaryl, —S(O)$_2$-alkylene-aryl, —S(O)$_2$-alkylene-heteroaryl, —Si(alkyl)$_2$, —Si(aryl)$_2$, —Si(heteroaryl)$_2$, —Si(alkyl)(aryl), —Si(alkyl)(cycloalkyl), —Si(alkyl)(heteroaryl), cycloalkyl, heterocycloalkyl, —O—C(O)-alkyl, —O—C(O)-aryl, —O—C(O)-cycloalkyl, —C(=N—CN)—NH$_2$, —C(=NH)—NH$_2$, —C(=NH)—NH(alkyl), —N(Y$_1$)(Y$_2$), -alkylene-N(Y$_1$)(Y$_2$), —C(O)N(Y$_1$)(Y$_2$) and —S(O)$_2$N(Y$_1$)(Y$_2$), wherein Y$_1$ and Y$_2$ can be the same or different and are independently selected from the group consisting of hydrogen, alkyl, aryl, cycloalkyl, and -alkylene-aryl. "Ring system substituent" may also mean a single moiety which simultaneously replaces two available hydrogens on two adjacent carbon atoms (one H on each carbon) on a ring system. Examples of such moiety are methylenedioxy, ethylenedioxy, —C(CH$_3$)$_2$— and the like which form moieties such as, for example:

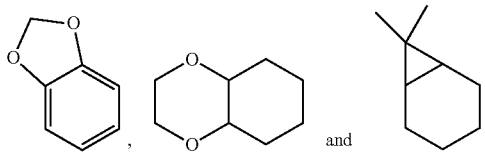

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "in substantially purified form," as used herein, refers to the physical state of a compound after the compound is isolated from a synthetic process (e.g., from a reaction mixture), a natural source, or a combination thereof. The term "in substantially purified form," also refers to the physical state of a compound after the compound is obtained from a purification process or processes described herein or well-known to the skilled artisan (e.g., chromatography, recrystallization and the like), in sufficient purity to be characterizable by standard analytical techniques described herein or well-known to the skilled artisan.

It should also be noted that any carbon as well as heteroatom with unsatisfied valences in the text, schemes, examples and tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in Organic Synthesis* (1991), Wiley, N.Y.

When any substituent or variable (e.g., alkyl, R$^6$, R$^a$, etc.) occurs more than one time in any constituent or in Formula (I), its definition on each occurrence is independent of its definition at every other occurrence, unless otherwise indicated.

As used herein, the term "composition" is intended to encompass a product comprising the specified ingredients in the specified amounts, as well as any product which results directly from combination of the specified ingredients in the specified amounts.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g., a drug precursor) that is transformed in vivo to provide a Cyclic Phosphonate Substituted Nucleoside Derivative or a pharmaceutically acceptable salt of the compound. The transformation may occur by various mechanisms (e.g., by metabolic or chemical processes), such as, for example, through hydrolysis in blood.

For example, if a Cyclic Phosphonate Substituted Nucleoside Derivative or a pharmaceutically acceptable salt, hydrate or solvate of the compound contains a carboxylic acid functional group, a prodrug can comprise an ester formed by the replacement of the hydrogen atom of the acid group with a group such as, for example, (C$_1$-C$_8$)alkyl, (C$_2$-C$_{12}$)alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as β-dimethylaminoethyl), carbamoyl-($C_1$-$C_2$)alkyl, N,N-di($C_1$-$C_2$)alkylcarbamoyl-($C_1$-$C_2$)alkyl and piperidino-, pyrrolidino- or morpholino($C_2$-$C_3$)alkyl, and the like.

Similarly, if a Cyclic Phosphonate Substituted Nucleoside Derivative contains an alcohol functional group, a prodrug can be formed by the replacement of one or more of the hydrogen atoms of the alcohol groups with a group such as, for example, ($C_1$-$C_6$)alkanoyloxymethyl, 1-(($C_1$-$C_6$)alkanoyloxy)ethyl, 1-methyl-1-(($C_1$-$C_6$)alkanoyloxy)ethyl, ($C_1$-$C_6$)alkoxycarbonyloxymethyl, N—($C_1$-$C_6$)alkoxycarbonylaminomethyl, succinoyl, ($C_1$-$C_6$)alkanoyl, α-amino ($C_1$-$C_4$)alkyl, α-amino($C_1$-$C_4$)alkylene-aryl, arylacyl and α-aminoacyl, or α-aminoacyl-α-aminoacyl, where each α-aminoacyl group is independently selected from the naturally occurring L-amino acids, or glycosyl (the radical resulting from the removal of a hydroxyl group of the hemiacetal form of a carbohydrate). Other non-limiting example of alcohol-derived prodrugs include —P(O)(OH)$_2$; —P(O)(—O—$C_1$-$C_6$alkyl)$_2$; —P(O)(—NH-(α-aminoacyl group))(-O-aryl); —P(O)(—O—($C_1$-$C_6$ alkylene)-S-acyl)(-NH-arylalkyl); and those described in U.S. Pat. No. 7,879,815; International Publication Nos. WO2005/003047, WO2008/082602, WO2010/0081628, WO2010/075517 and WO2010/075549; Mehellou, *Chem. Med. Chem.*, 5:1841-1842 (2005); Bobeck et al., *Antiviral Therapy* 15:935-950 (2010); Furman et al., Future Medicinal Chemistry, 1:1429-1452 (2009); and Erion, *Microsomes and Drug Oxidations, Proceedings of the International Symposium,* 17th, Saratoga Springs, N.Y., United States, Jul. 6-10, 2008, 7-12 (2008).

If a Cyclic Phosphonate Substituted Nucleoside Derivative incorporates an amine functional group, a prodrug can be formed by the replacement of a hydrogen atom in the amine group with a group such as, for example, R-carbonyl-, RO-carbonyl-, NRR'-carbonyl- wherein R and R' are each independently ($C_1$-$C_{10}$)alkyl, ($C_3$-$C_7$) cycloalkyl, benzyl, a natural α-aminoacyl, —C(OH)C(O)OY$^1$ wherein Y$^1$ is H, ($C_1$-$C_6$)alkyl or benzyl, —C(OY$^2$)Y$^3$ wherein Y$^2$ is ($C_1$-$C_4$) alkyl and Y$^3$ is ($C_1$-$C_6$)alkyl; carboxy ($C_1$-$C_6$)alkyl; amino ($C_1$-$C_4$)alkyl or mono-N- or di-N,N—($C_1$-$C_6$)alkylaminoalkyl; —C(Y$^4$)Y$^5$ wherein Y$^4$ is H or methyl and Y$^5$ is mono-N- or di-N,N—($C_1$-$C_6$)alkylamino morpholino; piperidin-1-yl or pyrrolidin-1-yl, and the like.

Pharmaceutically acceptable esters of the present compounds include the following groups: (1) carboxylic acid esters obtained by esterification of the hydroxy group of a hydroxyl compound, in which the non-carbonyl moiety of the carboxylic acid portion of the ester grouping is selected from straight or branched chain alkyl (e.g., methyl, ethyl, n-propyl, isopropyl, t-butyl, sec-butyl or n-butyl), alkoxyalkyl (e.g., methoxymethyl), aralkyl (e.g., benzyl), aryloxyalkyl (for example, phenoxymethyl), aryl (e.g., phenyl optionally substituted with, for example, halogen, $C_{1-4}$alkyl, —O—($C_{1-4}$alkyl) or amino); (2) sulfonate esters, such as alkyl- or aralkylsulfonyl (for example, methanesulfonyl); (3) amino acid esters (e.g., L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di($C_{6-24}$)acyl glycerol.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of solvates include ethanolates, methanolates, and the like. A "hydrate" is a solvate wherein the solvent molecule is water.

One or more compounds of the invention may optionally be converted to a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTechours.*, 5(1), article 12 (2004); and A. L. Bingham et al, *Chem. Commun.,* 603-604 (2001). A typical, non-limiting, process involves dissolving the inventive compound in desired amounts of the desired solvent (organic or water or mixtures thereof) at a higher than room temperature, and cooling the solution at a rate sufficient to form crystals which are then isolated by standard methods. Analytical techniques such as, for example IR spectroscopy, show the presence of the solvent (or water) in the crystals as a solvate (or hydrate).

The Cyclic Phosphonate Substituted Nucleoside Derivatives can form salts which are also within the scope of this invention. Reference to a Cyclic Phosphonate Substituted Nucleoside Derivative herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a Cyclic Phosphonate Substituted Nucleoside Derivative contains both a basic moiety, such as, but not limited to a pyridine or imidazole, and an acidic moiety, such as, but not limited to a carboxylic acid, zwitterions ("inner salts") may be formed and are included within the term "salt(s)" as used herein. In one embodiment, the salt is a pharmaceutically acceptable (i.e., non-toxic, physiologically acceptable) salt. In another embodiment, the salt is other than a pharmaceutically acceptable salt. Salts of the Compounds of Formula (I) may be formed, for example, by reacting a Cyclic Phosphonate Substituted Nucleoside Derivative with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use.* (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in

*The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamine, t-butyl amine, choline, and salts with amino acids such as arginine, lysine and the like. Basic nitrogen-containing groups may be quarternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Diastereomeric mixtures can be separated into their individual diastereomers on the basis of their physical chemical differences by methods well-known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Sterochemically pure compounds may also be prepared by using chiral starting materials or by employing salt resolution techniques. Also, some of the Cyclic Phosphonate Substituted Nucleoside Derivatives may be atropisomers (e.g., substituted biaryls) and are considered as part of this invention. Enantiomers can also be directly separated using chiral chromatographic techniques.

It is also possible that the Cyclic Phosphonate Substituted Nucleoside Derivatives may exist in different tautomeric forms, and all such forms are embraced within the scope of the invention. For example, all keto-enol and imine-enamine forms of the compounds are included in the invention.

All stereoisomers (for example, geometric isomers, optical isomers and the like) of the present compounds (including those of the salts, solvates, hydrates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. If a Cyclic Phosphonate Substituted Nucleoside Derivative incorporates a double bond or a fused ring, both the cis- and trans-forms, as well as mixtures, are embraced within the scope of the invention.

Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate", "ester", "prodrug" and the like, is intended to apply equally to the salt, solvate, ester and prodrug of enantiomers, stereoisomers, rotamers, tautomers, positional isomers, racemates or prodrugs of the inventive compounds.

In the Compounds of Formula (I), the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched Compounds of Formula (I) can be prepared without undue experimentation by conventional techniques well known to those skilled in the art or by processes analogous to those described in the Schemes and Examples herein using appropriate isotopically-enriched reagents and/or intermediates. In one embodiment, a Compound of Formula (I) has one or more of its hydrogen atoms replaced with deuterium.

Polymorphic forms of the Cyclic Phosphonate Substituted Nucleoside Derivatives, and of the salts, solvates, hydrates, esters and prodrugs of the Cyclic Phosphonate Substituted Nucleoside Derivatives, are intended to be included in the present invention.

The following abbreviations are used below and have the following meanings: Ac is acetyl or —C(O)CH$_3$, Bu is butyl; DCM is dichloromethane; DMSO is dimethyl sulfoxide; EDTA is ethylenediamine tetraacetic acid; EGTA is ethylene glycol tetraacetic acid; EtOAc is ethyl acetate; HPLC is high performance liquid chromatography; LCMS is liquid chromatography/mass spectrometry; MeOH is methanol; NMI is N-methylimidazole; NTP is nucleoside triphosphate; Pd/C is palladium on carbon; Pd(OH)$_2$/C is palladium hydroxide on carbon; TFA is trifluoroacetic acid; THF is tetrahydrofuran; and TLC is thin-layer chromatography.

The Compounds of Formula (I)

The present invention provides Cyclic Phosphonate Substituted Nucleoside Derivatives of Formula (I):

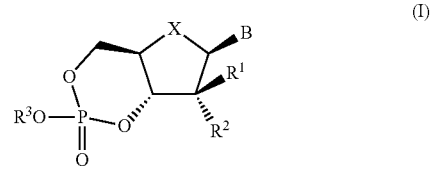

(I)

and pharmaceutically acceptable salts thereof, wherein B, X, R$^1$, R$^2$ and R$^3$ are defined above for the Compounds of Formula (I).

In one embodiment, X is O.
In another embodiment, X is N.
In another embodiment, X is S.
In another embodiment, X is CH$_2$.
In one embodiment, R$^1$ is C$_1$-C$_3$ alkyl.
In another embodiment, R$^1$ is methyl.
In one embodiment, R$^2$ is —NH$_2$.

In one embodiment, the compounds of formula (I) have the formula (Ia):

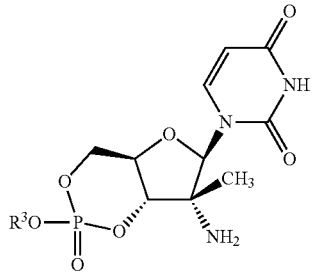

or a pharmaceutically acceptable salt thereof,
wherein:

$R^3$ is $C_6$-$C_{20}$ alkyl, —($C_1$-$C_3$ alkylene)$_m$-($C_6$-$C_{10}$ aryl) or $C_3$-$C_7$ cycloalkyl.

In one embodiment, for the compounds of Formula (I) or Formula (Ia), $R^3$ is $C_6$-$C_{20}$ alkyl, $C_3$-$C_7$ cycloalkyl or —($C_1$-$C_3$ alkylene)$_m$-($C_6$-$C_{10}$ aryl); wherein said $C_6$-$C_{20}$ alkyl group, said $C_3$-$C_7$ cycloalkyl group and said $C_6$-$C_{10}$ aryl group can be optionally substituted with up to five groups, each independently selected from $C_1$-$C_6$ alkyl, $C_2$-$C_6$ alkenyl, $C_2$-$C_6$ alkynyl, $C_3$-$C_7$ cycloalkyl, $C_6$-$C_{10}$ aryl, 5- or 6-membered monocyclic heteroaryl, 9- or 10-membered bicyclic heteroaryl, halo, —$OR^7$, —$SR^7$, —$S(O)R^7$, —$S(O)_2R^7$, —$S(O)_2N(R^7)_2$, $C_1$-$C_6$ haloalkyl, $C_1$-$C_6$ hydroxyalkyl, —O—($C_1$-$C_6$ haloalkyl), —CN, —$NO_2$, —$N(R^7)_2$, —$C(O)OR^7$, —$C(O)N(R^7)_2$ and —$NHC(O)R^7$, —$NHC(O)OR^7$ and —$NHC(O)N(R^7)_2$.

In another embodiment, for the compounds of Formula (I) or Formula (Ia), $R^3$ is $C_6$-$C_{20}$ alkyl, $C_3$-$C_7$ cycloalkyl or benzyl, wherein said $C_6$-$C_{20}$ alkyl group, said $C_3$-$C_7$ cycloalkyl group and the phenyl moiety of said benzyl can be optionally substituted with up to five groups, each independently selected from $C_1$-$C_6$ alkyl, $C_2$-$C_6$ alkenyl, $C_2$-$C_6$ alkynyl, $C_3$-$C_7$ cycloalkyl, $C_6$-$C_{10}$ aryl, 5- or 6-membered monocyclic heteroaryl, 9- or 10-membered bicyclic heteroaryl, halo, —$OR^7$, —$SR^7$, —$S(O)R^7$, —$S(O)_2R^7$, —$S(O)_2N(R^7)_2$, $C_1$-$C_6$ haloalkyl, $C_1$-$C_6$ hydroxyalkyl, —O—($C_1$-$C_6$ haloalkyl), —CN, —$NO_2$, —$N(R^7)_2$, —$C(O)OR^7$, —$C(O)N(R^7)_2$ and —$NHC(O)R^7$, —$NHC(O)OR^7$ and —$NHC(O)N(R^7)_2$.

In another embodiment, for the compounds of Formula (I) or Formula (Ia), $R^3$ is H, $C_7$-$C_{20}$ alkyl, —($C_1$-$C_3$ alkylene)$_m$-($C_3$-$C_7$ cycloalkyl) or —($C_1$-$C_3$ alkylene)$_m$-($C_6$-$C_{10}$ aryl); wherein said $C_7$-$C_{20}$ alkyl group, said $C_3$-$C_7$ cycloalkyl group and said $C_6$-$C_{10}$ aryl group can be optionally substituted with up to five groups, each independently selected from $C_1$-$C_6$ alkyl, $C_2$-$C_6$ alkenyl, $C_2$-$C_6$ alkynyl, $C_3$-$C_7$ cycloalkyl, $C_6$-$C_{10}$ aryl, 5- or 6-membered monocyclic heteroaryl, 9- or 10-membered bicyclic heteroaryl, halo, —$OR^7$, —$SR^7$, —$S(O)R^7$, —$S(O)_2R^7$, —$S(O)_2N(R^7)_2$, $C_1$-$C_6$ haloalkyl, $C_1$-$C_6$ hydroxyalkyl, —O—($C_1$-$C_6$ haloalkyl), —CN, —$NO_2$, —$N(R^7)_2$, —$C(O)OR^7$, —$C(O)N(R^7)_2$ and —$NHC(O)R^7$, —$NHC(O)OR^7$ and —$NHC(O)N(R^7)_2$.

In another embodiment, for the compounds of Formula (I) or Formula (Ia), $R^3$ is $C_7$-$C_{20}$ alkyl, $C_3$-$C_7$ cycloalkyl or benzyl, wherein said $C_7$-$C_{20}$ alkyl group, said $C_3$-$C_7$ cycloalkyl group and the pheny moiety of said benzyl can be optionally substituted with up to five groups, each independently selected from $C_1$-$C_6$ alkyl, $C_2$-$C_6$ alkenyl, $C_2$-$C_6$ alkynyl, $C_3$-$C_7$ cycloalkyl, $C_6$-$C_{10}$ aryl, 5- or 6-membered monocyclic heteroaryl, 9- or 10-membered bicyclic heteroaryl, halo, —$OR^7$, —$SR^7$, —$S(O)R^7$, —$S(O)_2R^7$, —$S(O)_2N(R^7)_2$, $C_1$-$C_6$ haloalkyl, $C_1$-$C_6$ hydroxyalkyl, —O—($C_1$-$C_6$ haloalkyl), —CN, —$NO_2$, —$N(R^7)_2$, —$C(O)OR^7$, —$C(O)N(R^7)_2$ and —$NHC(O)R^7$, —$NHC(O)OR^7$ and —$NHC(O)N(R^7)_2$.

In one embodiment, for the compounds of Formula (I) or Formula (Ia), $R^3$ is $C_7$-$C_{20}$ alkyl, —($C_1$-$C_3$ alkylene)$_m$-($C_6$-$C_{10}$ aryl) or $C_3$-$C_7$ cycloalkyl.

In another embodiment, for the compounds of Formula (I) or Formula (Ia), $R^3$ is $C_6$-$C_{20}$ alkyl.

In another embodiment, for the compounds of Formula (I) or Formula (Ia), $R^3$ is $C_7$-$C_{20}$ alkyl.

In still another embodiment, for the compounds of Formula (I) or Formula (Ia), $R^3$ is —($C_1$-$C_3$ alkylene)$_m$-($C_6$-$C_{10}$ aryl).

In another embodiment, for the compounds of Formula (I) or Formula (Ia), $R^3$ is —($C_1$-$C_3$ alkylene)$_m$-($C_3$-$C_7$ cycloalkyl).

In another embodiment, for the compounds of Formula (I) or Formula (Ia), $R^3$ is $C_3$-$C_7$ cycloalkyl.

In yet another embodiment, for the compounds of Formula (I) or Formula (Ia), $R^3$ is cyclobutyl, cyclopentyl, benzyl, —$CH_2CH(CH_2CH_2CH_3)_2$ or —$CH_2CH(CH_2CH_3)_2$.

In another embodiment, for the compounds of Formula (I) or Formula (Ia), $R^3$ is cyclobutyl.

In another embodiment, for the compounds of Formula (I) or Formula (Ia), $R^3$ is cyclopentyl.

In a further embodiment, for the compounds of Formula (I) or Formula (Ia), $R^3$ is benzyl.

In another embodiment, for the compounds of Formula (I) or Formula (Ia), $R^3$ is —$CH_2CH(CH_2CH_2CH_3)_2$.

In another embodiment, for the compounds of Formula (I) or Formula (Ia), $R^3$ is —$CH_2CH(CH_2CH_3)_2$.

In one embodiment, variables B, X, $R^1$, $R^2$ and $R^3$ for the Compounds of Formula (I) are selected independently of each other.

In another embodiment, the Compounds of Formula (I) are in substantially purified form.

The Compounds of Formula (I) may be referred to herein by chemical structure and/or by chemical name. In the instance that both the structure and the name of a Compound of Formula (I) are provided and a discrepancy is found to exist between the chemical structure and the corresponding chemical name, it is understood that the chemical structure will predominate.

Other embodiments of the present invention include the following:

(a) A pharmaceutical composition comprising an effective amount of a Compound of Formula (I) or a pharmaceutically acceptable salt thereof, and a pharmaceutically acceptable carrier.

(b) The pharmaceutical composition of (a), further comprising a second therapeutic agent selected from the group consisting of HCV antiviral agents, immunomodulators, and anti-infective agents.

(c) The pharmaceutical composition of (b), wherein the HCV antiviral agent is an antiviral selected from the group consisting of HCV protease inhibitors, HCV NS5B polymerase inhibitors and HCV NS5A inhibitors.

(d) A pharmaceutical combination that is (i) a Compound of Formula (I) and (ii) a second therapeutic agent selected from the group consisting of HCV antiviral agents, immunomodulators, and anti-infective agents; wherein the Compound of Formula (I) and the second therapeutic agent are each employed in an amount that renders the combination effective for inhibiting HCV replication, or for treating HCV infection and/or reducing the likelihood or severity of symptoms of HCV infection.

(e) The combination of (d), wherein the HCV antiviral agent is an antiviral selected from the group consisting of HCV protease inhibitors, HCV NS5B polymerase inhibitors and HCV NS5A inhibitors.

(f) A method of inhibiting HCV replication in a subject in need thereof which comprises administering to the subject an effective amount of a Compound of Formula (I).

(g) A method of treating HCV infection and/or reducing the likelihood or severity of symptoms of HCV infection in a subject in need thereof which comprises administering to the subject an effective amount of a Compound of Formula (I).

(h) The method of (g), wherein the Compound of Formula (I) is administered in combination with an effective amount of at least one second therapeutic agent selected from the group consisting of HCV antiviral agents, immunomodulators, and anti-infective agents.

(i) The method of (h), wherein the HCV antiviral agent is an antiviral selected from the group consisting of HCV protease inhibitors, HCV NS5B polymerase inhibitors and HCV NS5A inhibitors.

(j) A method of inhibiting HCV replication in a subject in need thereof which comprises administering to the subject the pharmaceutical composition of (a), (b) or (c) or the combination of (d) or (e).

(k) A method of treating HCV infection and/or reducing the likelihood or severity of symptoms of HCV infection in a subject in need thereof which comprises administering to the subject the pharmaceutical composition of (a), (b) or (c) or the combination of (d) or (e).

Additional embodiments of the invention include the pharmaceutical compositions, combinations and methods set forth in (a)-(k) above and the uses set forth in the discussion below, wherein the compound of the present invention employed therein is a compound of one of the embodiments, aspects, classes, sub-classes, or features of the compounds described above. In all of these embodiments, the compound may optionally be used in the form of a pharmaceutically acceptable salt or hydrate as appropriate. It is understood that references to compounds would include the compound in its present form as well as in different forms, such as polymorphs, solvates and hydrates, as applicable.

It is further to be understood that the embodiments of compositions and methods provided as (a) through (k) above are understood to include all embodiments of the compounds, including such embodiments as result from combinations of embodiments.

Uses of the Cyclic Phosphonate Substituted Nucleoside Derivatives

Treatment or Prevention of HCV Infection

The Cyclic Phosphonate Substituted Nucleoside Derivatives are useful in the inhibition of HCV, the treatment of HCV infection and/or reduction of the likelihood or severity of symptoms of HCV infection and the inhibition of HCV viral replication and/or HCV viral production in a cell-based system. For example, the Cyclic Phosphonate Substituted Nucleoside Derivatives are useful in treating infection by HCV after suspected past exposure to HCV by such means as blood transfusion, exchange of body fluids, bites, accidental needle stick, or exposure to patient blood during surgery or other medical procedures.

In one embodiment, the hepatitis C infection is acute hepatitis C. In another embodiment, the hepatitis C infection is chronic hepatitis C.

Accordingly, in one embodiment, the invention provides methods for treating HCV infection in a patient, the methods comprising administering to the patient an effective amount of at least one Cyclic Phosphonate Substituted Nucleoside Derivative or a pharmaceutically acceptable salt thereof. In a specific embodiment, the amount administered is effective to treat or prevent infection by HCV in the patient. In another specific embodiment, the amount administered is effective to inhibit HCV viral replication and/or viral production in the patient.

The Cyclic Phosphonate Substituted Nucleoside Derivatives are also useful in the preparation and execution of screening assays for antiviral compounds. For example the Cyclic Phosphonate Substituted Nucleoside Derivatives are useful for identifying resistant HCV replicon cell lines harboring mutations within NS5B, which are excellent screening tools for more powerful antiviral compounds. Furthermore, the Cyclic Phosphonate Substituted Nucleoside Derivatives are useful in establishing or determining the binding site of other antivirals to the HCV NS5B polymerase.

The compositions and combinations of the present invention can be useful for treating a patient suffering from infection related to any HCV genotype. HCV types and subtypes may differ in their antigenicity, level of viremia, severity of disease produced, and response to interferon therapy as described in Holland et al., *Pathology*, 30(2):192-195 (1998). The nomenclature set forth in Simmonds et al., *J Gen Virol*, 74(Pt11):2391-2399 (1993) is widely used and classifies isolates into six major genotypes, 1 through 6, with two or more related subtypes, e.g., 1a and 1b.

Combination Therapy

In another embodiment, the present methods for treating or preventing HCV infection can further comprise the administration of one or more additional therapeutic agents which are not Cyclic Phosphonate Substituted Nucleoside Derivatives.

In one embodiment, the additional therapeutic agent is an antiviral agent.

In another embodiment, the additional therapeutic agent is an immunomodulatory agent, such as an immunosuppressive agent.

Accordingly, in one embodiment, the present invention provides methods for treating a viral infection in a patient, the method comprising administering to the patient: (i) at least one Cyclic Phosphonate Substituted Nucleoside Derivative (which may include two or more different 2'-Substituted Nucleoside Derivatives), or a pharmaceutically acceptable salt thereof, and (ii) at least one additional therapeutic agent that is other than a Cyclic Phosphonate Substituted Nucleoside Derivative, wherein the amounts administered are together effective to treat or prevent a viral infection.

When administering a combination therapy of the invention to a patient, therapeutic agents in the combination, or a pharmaceutical composition or compositions comprising therapeutic agents, may be administered in any order such as, for example, sequentially, concurrently, together, simultaneously and the like. The amounts of the various actives in such combination therapy may be different amounts (different dosage amounts) or same amounts (same dosage amounts). Thus, for non-limiting illustration purposes, a Cyclic Phosphonate Substituted Nucleoside Derivative and an additional therapeutic agent may be present in fixed amounts (dosage amounts) in a single dosage unit (e.g., a capsule, a tablet and the like).

In one embodiment, the at least one Cyclic Phosphonate Substituted Nucleoside Derivative is administered during a time when the additional therapeutic agent(s) exert their prophylactic or therapeutic effect, or vice versa.

In another embodiment, the at least one Cyclic Phosphonate Substituted Nucleoside Derivative and the additional therapeutic agent(s) are administered in doses commonly employed when such agents are used as monotherapy for treating a viral infection.

In another embodiment, the at least one Cyclic Phosphonate Substituted Nucleoside Derivative and the additional therapeutic agent(s) are administered in doses lower than the doses commonly employed when such agents are used as monotherapy for treating a viral infection.

In still another embodiment, the at least one Cyclic Phosphonate Substituted Nucleoside Derivative and the additional therapeutic agent(s) act synergistically and are administered in doses lower than the doses commonly employed when such agents are used as monotherapy for treating a viral infection.

In one embodiment, the at least one Cyclic Phosphonate Substituted Nucleoside Derivative and the additional therapeutic agent(s) are present in the same composition. In one embodiment, this composition is suitable for oral administration. In another embodiment, this composition is suitable for intravenous administration. In another embodiment, this composition is suitable for subcutaneous administration. In still another embodiment, this composition is suitable for parenteral administration.

Viral infections and virus-related disorders that can be treated or prevented using the combination therapy methods of the present invention include, but are not limited to, those listed above.

In one embodiment, the viral infection is HCV infection.

The at least one Cyclic Phosphonate Substituted Nucleoside Derivative and the additional therapeutic agent(s) can act additively or synergistically. A synergistic combination may allow the use of lower dosages of one or more agents and/or less frequent administration of one or more agents of a combination therapy. A lower dosage or less frequent administration of one or more agents may lower toxicity of therapy without reducing the efficacy of therapy.

In one embodiment, the administration of at least one Cyclic Phosphonate Substituted Nucleoside Derivative and the additional therapeutic agent(s) may inhibit the resistance of a viral infection to these agents.

Non-limiting examples of additional therapeutic agents useful in the present compositions and methods include an interferon, an immunomodulator, a viral replication inhibitor, an antisense agent, a therapeutic vaccine, a viral polymerase inhibitor, a nucleoside inhibitor, a viral protease inhibitor, a viral helicase inhibitor, a virion production inhibitor, a viral entry inhibitor, a viral assembly inhibitor, an antibody therapy (monoclonal or polyclonal), and any agent useful for treating an RNA-dependent polymerase-related disorder.

In one embodiment, one or more compounds of the invention are administered with one or more additional therapeutic agents, including but not limited to the therapeutic agents described, supra.

In one embodiment, the additional therapeutic agent is a viral protease inhibitor.

In another embodiment, the additional therapeutic agent is a viral replication inhibitor.

In another embodiment, the additional therapeutic agent is an HCV NS3 protease inhibitor.

In still another embodiment, the additional therapeutic agent is an HCV NS5B polymerase inhibitor.

In another embodiment, the additional therapeutic agent is a nucleoside inhibitor.

In another embodiment, the additional therapeutic agent is an interferon.

In yet another embodiment, the additional therapeutic agent is an HCV replicase inhibitor.

In another embodiment, the additional therapeutic agent is an antisense agent.

In another embodiment, the additional therapeutic agent is a therapeutic vaccine.

In a further embodiment, the additional therapeutic agent is a virion production inhibitor.

In another embodiment, the additional therapeutic agent is an antibody therapy.

In another embodiment, the additional therapeutic agent is an HCV NS2 inhibitor.

In still another embodiment, the additional therapeutic agent is an HCV NS4A inhibitor.

In another embodiment, the additional therapeutic agent is an HCV NS4B inhibitor.

In another embodiment, the additional therapeutic agent is an HCV NS5A inhibitor In yet another embodiment, the additional therapeutic agent is an HCV NS3 helicase inhibitor.

In another embodiment, the additional therapeutic agent is an HCV IRES inhibitor.

In another embodiment, the additional therapeutic agent is an HCV p7 inhibitor.

In a further embodiment, the additional therapeutic agent is an HCV entry inhibitor.

In another embodiment, the additional therapeutic agent is an HCV assembly inhibitor.

In another embodiment, one or more compounds of the present invention are administered with one additional therapeutic agent selected from an HCV protease inhibitor, an interferon, a pegylated interferon and ribavirin. In another embodiment, one or more compounds of the present invention are administered with one additional therapeutic agent selected from an HCV polymerase inhibitor, a viral protease inhibitor, an interferon, and a viral replication inhibitor. In another embodiment, one or more compounds of the present invention are administered with ribavirin.

In still another embodiment, one or more compounds of the present invention are administered with two additional therapeutic agents selected from an HCV protease inhibitor, an HCV replication inhibitor, a nucleoside, an interferon, a pegylated interferon and ribavirin.

In another embodiment, one or more compounds of the present invention are administered with an HCV protease inhibitor and ribavirin. In another specific embodiment, one or more compounds of the present invention are administered with a pegylated interferon and ribavirin.

In another embodiment, one or more compounds of the present invention are administered with three additional therapeutic agents selected from an HCV protease inhibitor, an HCV replication inhibitor, a nucleoside, an interferon, a pegylated interferon and ribavirin.

In one embodiment, one or more compounds of the present invention are administered with two additional therapeutic agents selected from an HCV polymerase inhibitor, a viral protease inhibitor, an interferon, and a viral replication inhibitor.

In another embodiment, one or more compounds of the present invention are administered with ribavirin, interferon and another therapeutic agent.

In another embodiment, one or more compounds of the present invention are administered with ribavirin, interferon and another therapeutic agent, wherein the additional therapeutic agent is selected from an HCV polymerase inhibitor, a viral protease inhibitor, and a viral replication inhibitor.

In still another embodiment, one or more compounds of the present invention are administered with ribavirin, interferon and a viral protease inhibitor.

In another embodiment, one or more compounds of the present invention are administered with ribavirin, interferon and an HCV protease inhibitor.

In another embodiment, one or more compounds of the present invention are administered with ribavirin, interferon and boceprevir or telaprevir.

In a further embodiment, one or more compounds of the present invention are administered with ribavirin, interferon and an HCV polymerase inhibitor.

In another embodiment, one or more compounds of the present invention are administered with pegylated-interferon alpha and ribavirin.

In one embodiment, the additional therapeutic agents comprise a viral protease inhibitor and a viral polymerase inhibitor.

In still another embodiment, the additional therapeutic agents comprise a viral protease inhibitor and an immunomodulatory agent.

In yet another embodiment, the additional therapeutic agents comprise a polymerase inhibitor and an immunomodulatory agent.

In another embodiment, the additional therapeutic agents comprise a viral protease inhibitor and a nucleoside.

In another embodiment, the additional therapeutic agents comprise an immunomodulatory agent and a nucleoside.

In one embodiment, the additional therapeutic agents comprise an HCV protease inhibitor and an HCV polymerase inhibitor.

In another embodiment, the additional therapeutic agents comprise a nucleoside and an HCV NS5A inhibitor.

In another embodiment, the additional therapeutic agents comprise a viral protease inhibitor, an immunomodulatory agent and a nucleoside.

In a further embodiment, the additional therapeutic agents comprise a viral protease inhibitor, a viral polymerase inhibitor and an immunomodulatory agent.

In another embodiment, the additional therapeutic agent is ribavirin.

HCV polymerase inhibitors useful in the present compositions and methods include, but are not limited to, VP-19744 (Wyeth/ViroPharma), PSI-7851 (Pharmasset), RG7128 (Roche/Pharmasset), PSI-7977 (Pharmasset), PSI-938 (Pharmasset), PSI-879 (Pharmasset), PSI-661 (Pharmasset), PF-868554/filibuvir (Pfizer), VCH-759NX-759 (ViroChem Pharma/Vertex), HCV-371 (Wyeth/VirroPharma), HCV-796 (Wyeth/ViroPharma), IDX-184 (Idenix), IDX-375 (Idenix), NM-283 (Idenix/Novartis), GL-60667 (Genelabs), JTK-109 (Japan Tobacco), PSI-6130 (Pharmasset), R1479 (Roche), R-1626 (Roche), R-7128 (Roche), MK-0608 (Isis/Merck), INX-8014 (Inhibitex), INX-8018 (Inhibitex), INX-189 (Inhibitex), GS 9190 (Gilead), A-848837 (Abbott), ABT-333 (Abbott), ABT-072 (Abbott), A-837093 (Abbott), BI-207127 (Boehringer-Ingelheim), BILB-1941 (Boehringer-Ingelheim), MK-3281 (Merck), VCH-222/VX-222 (ViroChem/Vertex), VCH-916 (ViroChem), VCH-716(ViroChem), GSK-71185 (Glaxo SmithKline), ANA598 (Anadys), GSK-625433 (Glaxo SmithKline), XTL-2125 (XTL Biopharmaceuticals), and those disclosed in Ni et al., *Current Opinion in Drug Discovery and Development*, 7(4):446 (2004); Tan et al., *Nature Reviews*, 1:867 (2002); and Beaulieu et al., *Current Opinion in Investigational Drugs*, 5:838 (2004).

Other HCV polymerase inhibitors useful in the present compositions and methods include, but are not limited to, those disclosed in International Publication Nos. WO 08/082484, WO 08/082488, WO 08/083351, WO 08/136815, WO 09/032116, WO 09/032123, WO 09/032124 and WO 09/032125; and the following compounds:

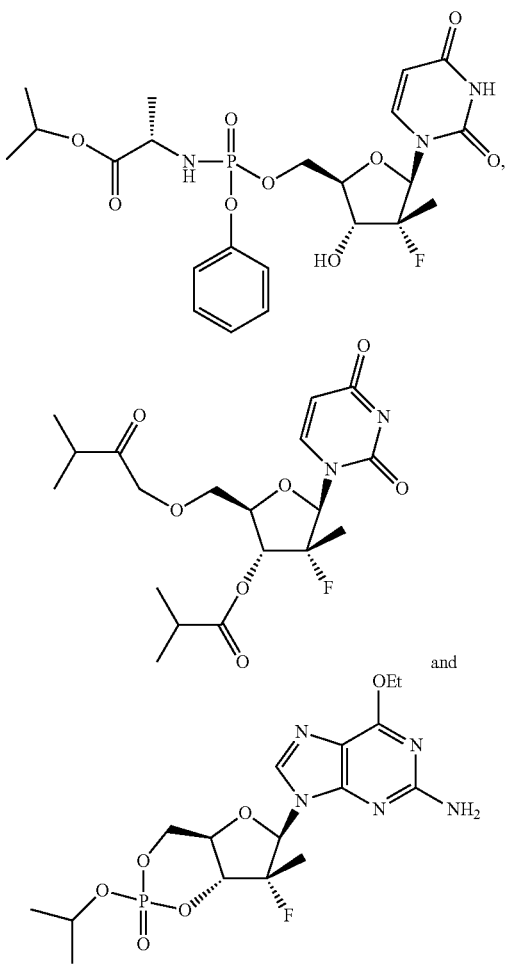

and pharmaceutically acceptable salts thereof.

Interferons useful in the present compositions and methods include, but are not limited to, interferon alfa-2a, interferon alfa-2b, interferon alfacon-1 and petroleum etherG-interferon alpha conjugates. "PEG-interferon alpha conjugates" are interferon alpha molecules covalently attached to a petroleum etherG molecule. Illustrative petroleum etherG-interferon alpha conjugates include interferon alpha-2a (Roferon™, Hoffman La-Roche, Nutley, N.J. in the form of pegylated interferon alpha-2a (e.g., as sold under the trade name Pegasys™), interferon alpha-2b (Intron™, from Schering-Plough Corporation) in the form of pegylated interferon alpha-2b (e.g., as sold under the trade name petroleum etherG-Intron™ from Schering-Plough Corporation), interferon alpha-2b-XL (e.g., as sold under the trade name petroleum etherG-Intron™), interferon alpha-2c (Berofor Alpha™, Boehringer Ingelheim, Ingelheim, Germany), petroleum etherG-interferon lambda (Bristol-Myers Squibb and ZymoGenetics), interferon alfa-2b alpha fusion polypeptides, interferon fused with the human blood protein albumin (Albuferon™, Human Genome Sciences), Omega Interferon (Intarcia), Locteron controlled release interferon (Biolex/OctoPlus), Biomed-510 (omega interferon), Peg-IL-29 (ZymoGenetics), Locteron CR (Octoplus), R-7025 (Roche), IFN-α-2b-XL (Flamel Technologies), belerofon (Nautilus) and consensus interferon as defined by determination of a consensus sequence of naturally occurring interferon alphas (Infergen™, Amgen, Thousand Oaks, Calif.).

Examples of viral protease inhbitors useful in the present compositions and methods include, but are not limited to, an HCV protease inhibitor. Examples of HCV protease inhibitors useful in the present compositions and methods include, but are not limited to, VX-950 (Telaprevir, Vertex), VX-500 (Vertex), VX-813 (Vertex), VBY-376 (Virobay), BI-201335 (Boehringer Ingelheim), TMC-435 (Medivir/Tibotec), ABT-450 (Abbott/Enanta), TMC-435350 (Medivir), RG7227 (Danoprevir, InterMune/Roche), EA-058 (Abbott/Enanta), EA-063 (Abbott/Enanta), GS-9256 (Gilead), IDX-320 (Idenix), ACH-1625 (Achillion), ACH-2684 (Achillion), GS-9132 (Gilead/Achillion), ACH-1095 (Gilead/Achillon), IDX-136 (Idenix), IDX-316 (Idenix), ITMN-8356 (InterMune), ITMN-8347 (InterMune), ITMN-8096 (InterMune), ITMN-7587 (InterMune), BMS-650032 (Bristol-Myers Squibb), VX-985 (Vertex) and PHX1766 (Phenomix).

Further examples of HCV protease inhibitors useful in the present compositions and methods include, but are not limited to, the following compounds:

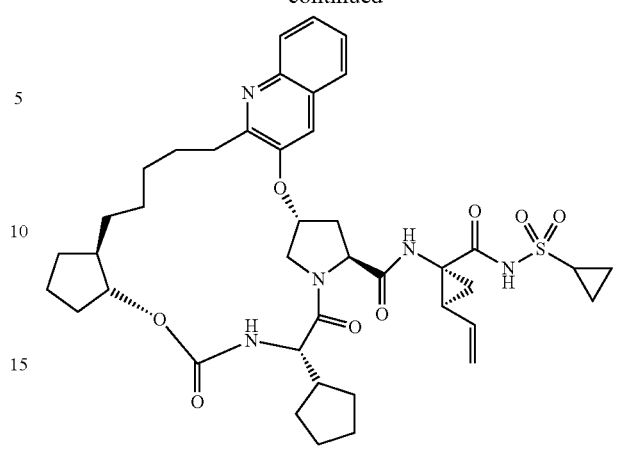

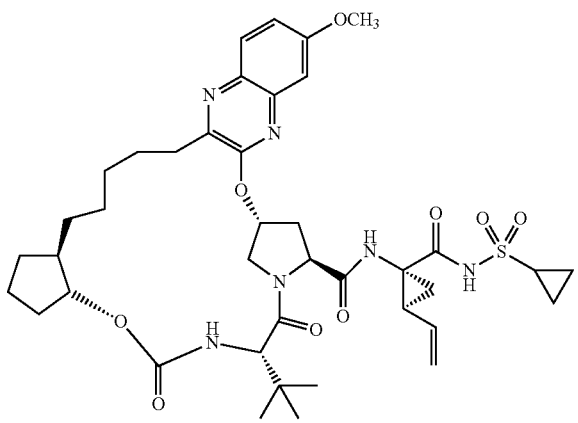

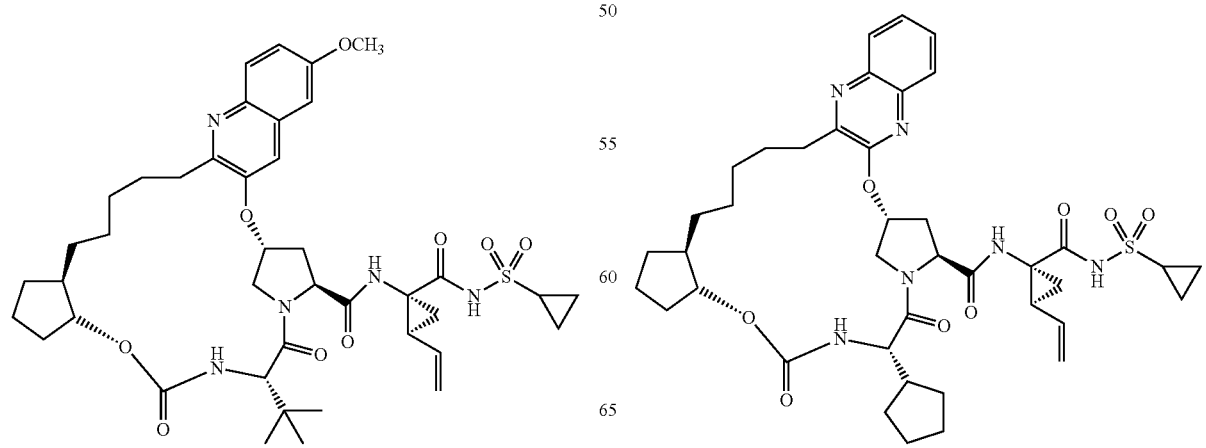

-continued
25
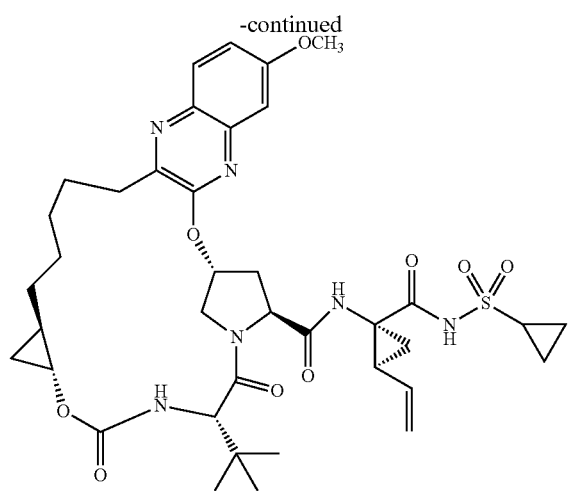
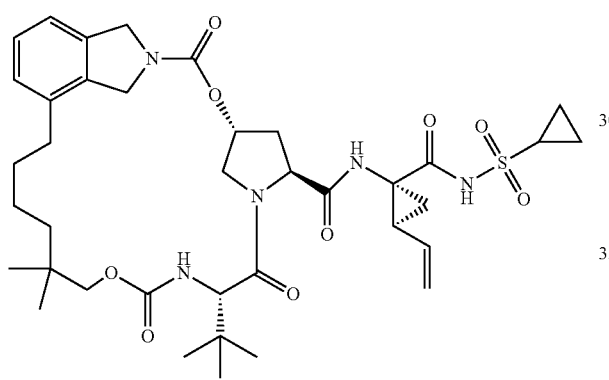
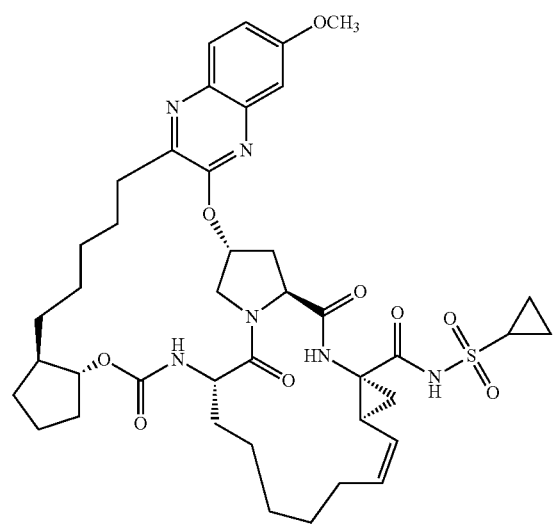
26
-continued
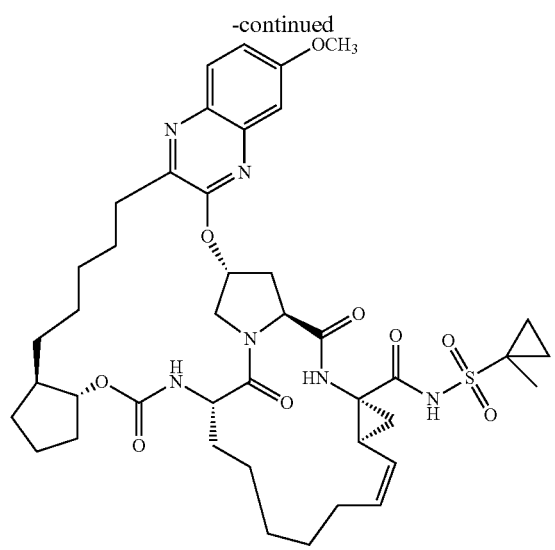
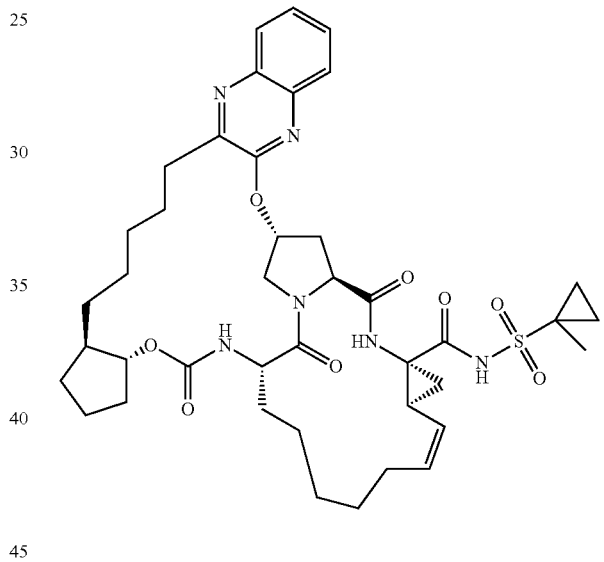
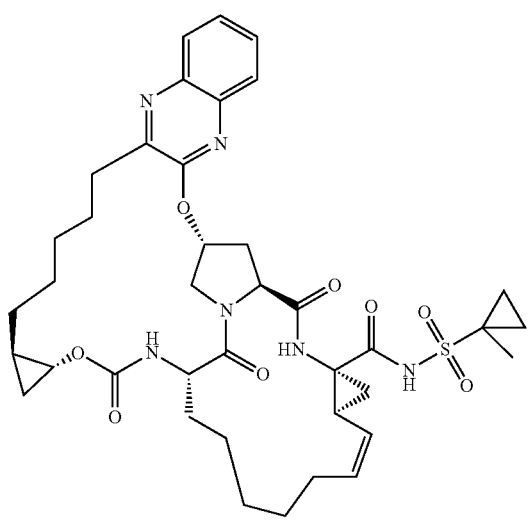

27
-continued
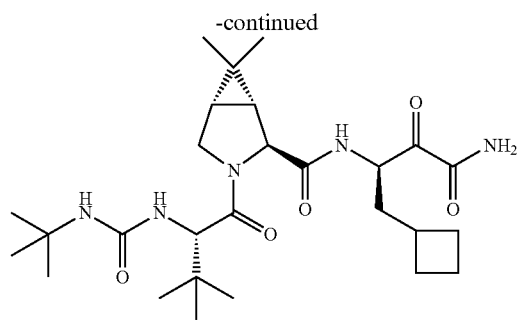
28
-continued
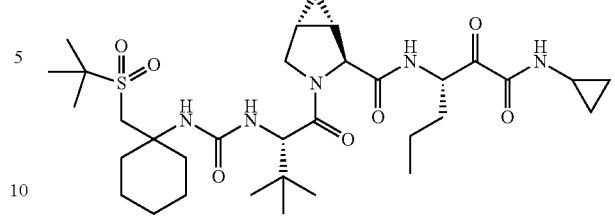
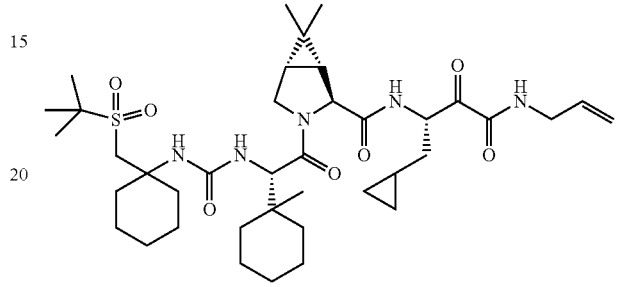
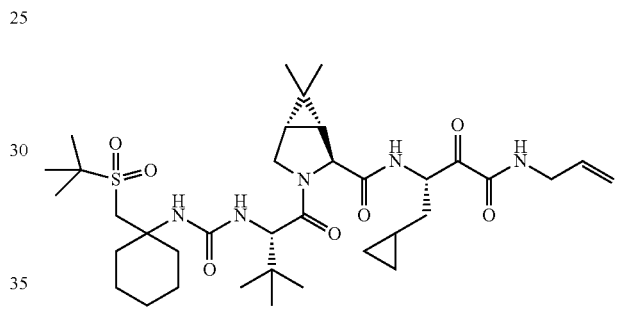
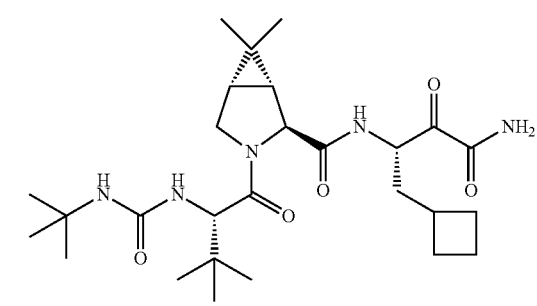
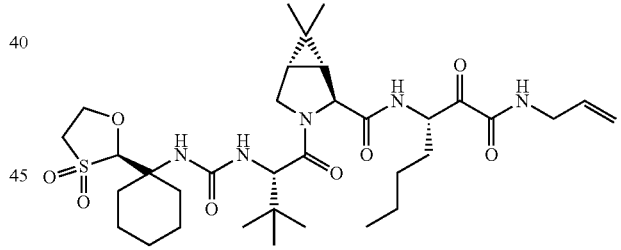
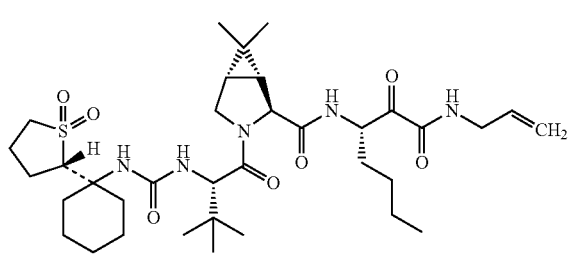
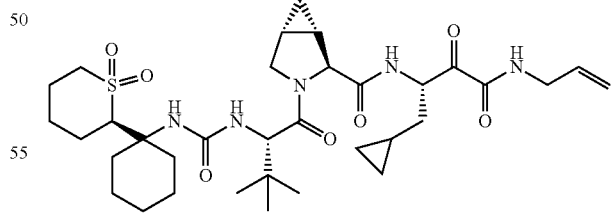
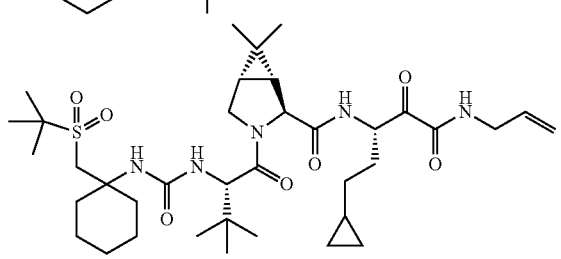
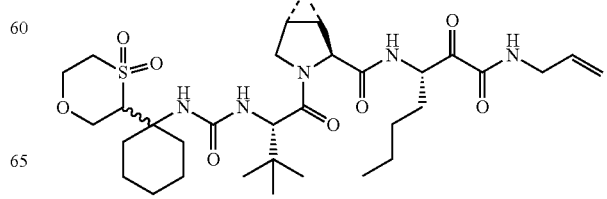

-continued

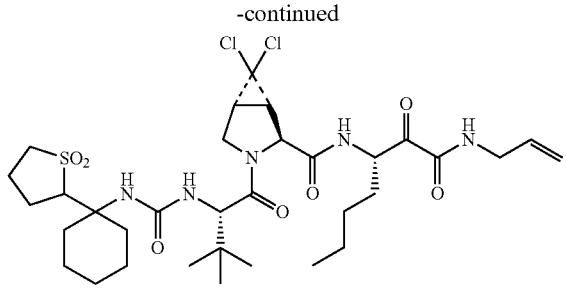

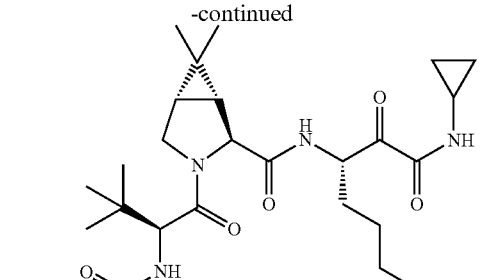

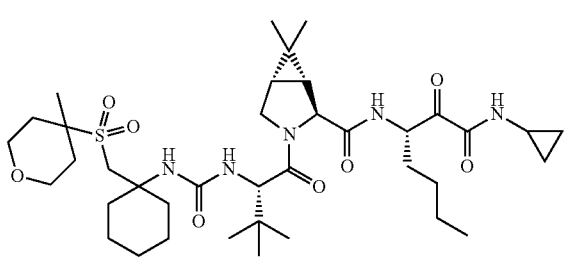

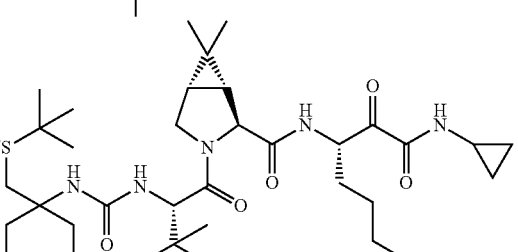

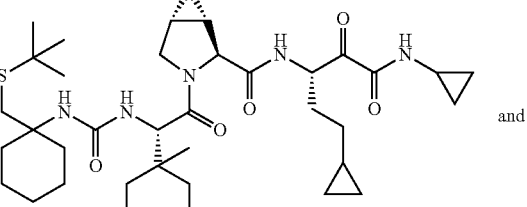

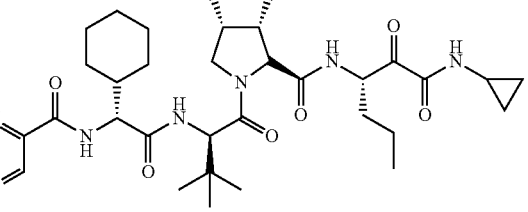

and

and pharmaceutically acceptable salts thereof.

Viral replication inhibitors useful in the present compositions and methods include, but are not limited to, HCV replicase inhibitors, IRES inhibitors, NS4A inhibitors, NS3 helicase inhibitors, NS5A inhibitors, NS5B inhibitors, ribavirin, AZD-2836 (Astra Zeneca), viramidine, A-831 (Arrow Therapeutics), EDP-239 (Enanta), ACH-2928 (Achillion), GS-5885 (Gilead); an antisense agent or a therapeutic vaccine.

HCV NS5A inhibitors useful in the present compositions and methods include, but are not limited to, ACH-2928 (Achilon), A-832 (Arrow Therpeutics), AZD-7295 (Astra Zeneca/Arrow), GS-5885 (Gilead), PPI-461 (Presidio), PPI-1301 (Presidio), BMS-824383 (Bristol-Myers Squibb) and BMS-790052 (Bristol-Myers Squibb). Additional HCV NS5A inhibitors useful as second additional therapeutic agents in the present compositions and methods include, but are not limited to those disclosed in International Publication No. WO 2010/111483 and the following compounds:
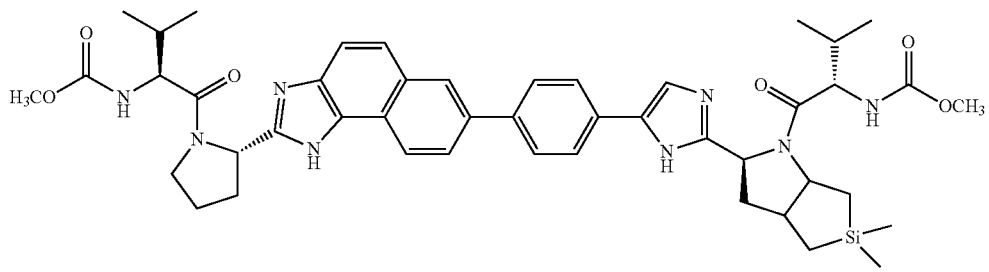
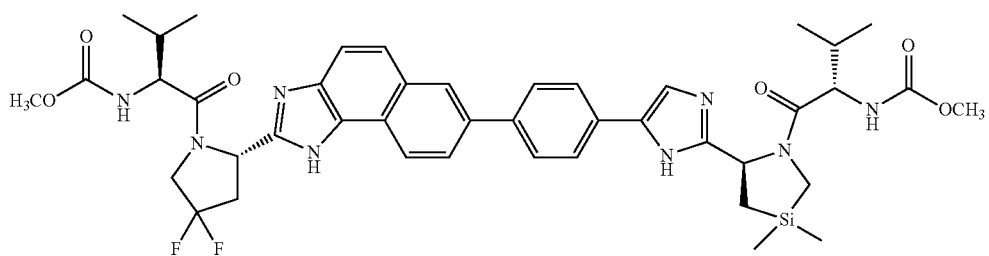
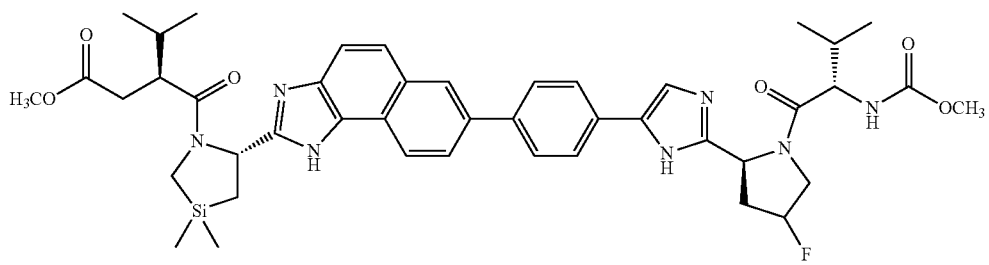
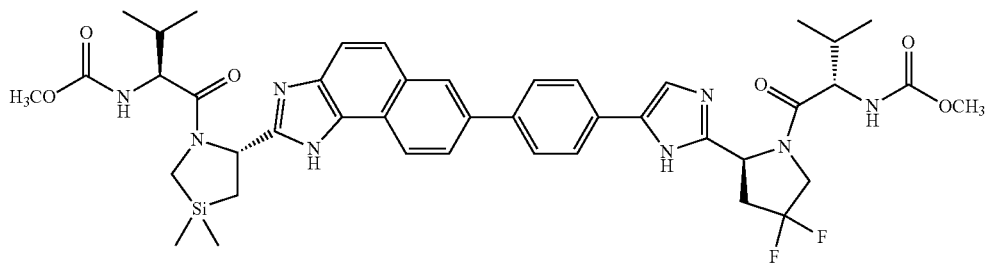
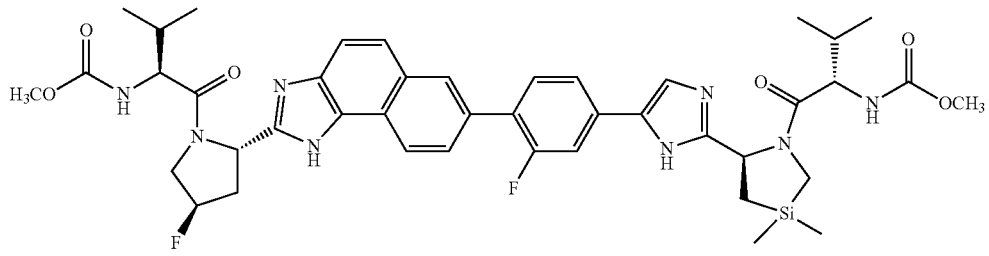
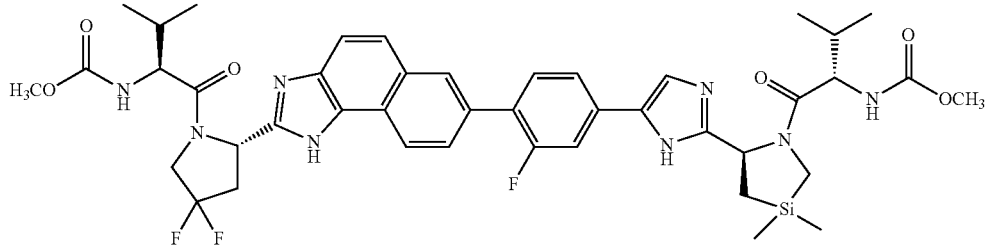

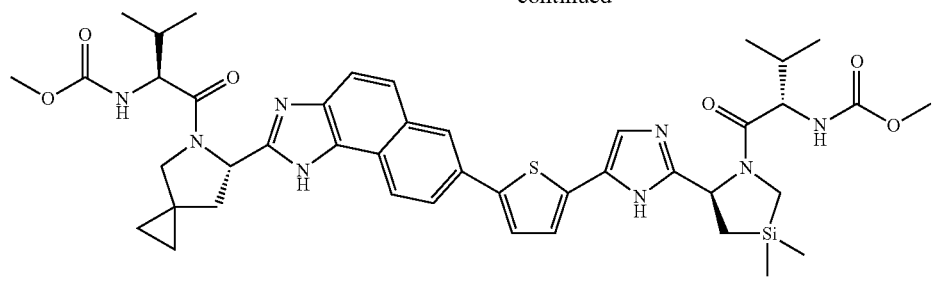
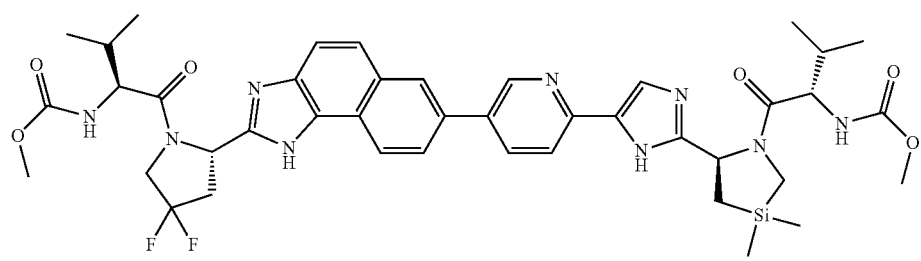
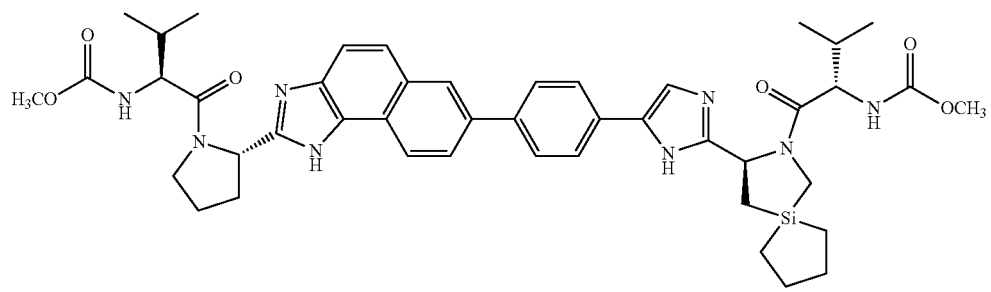
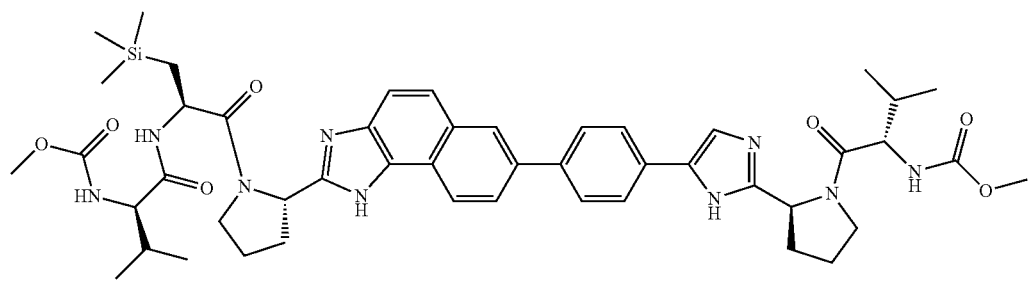
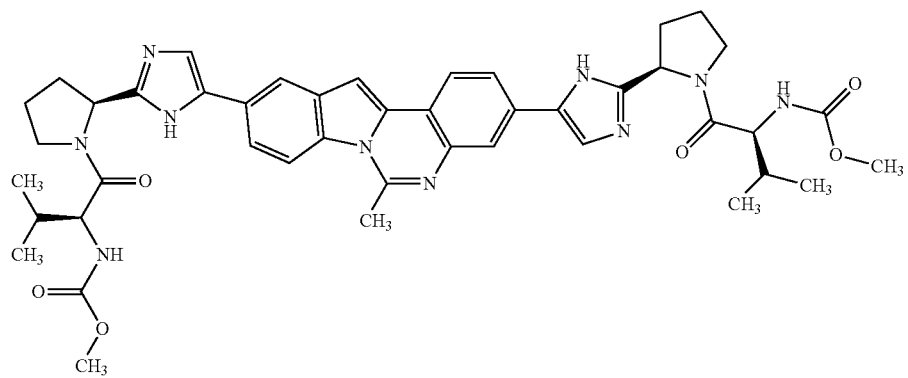

-continued
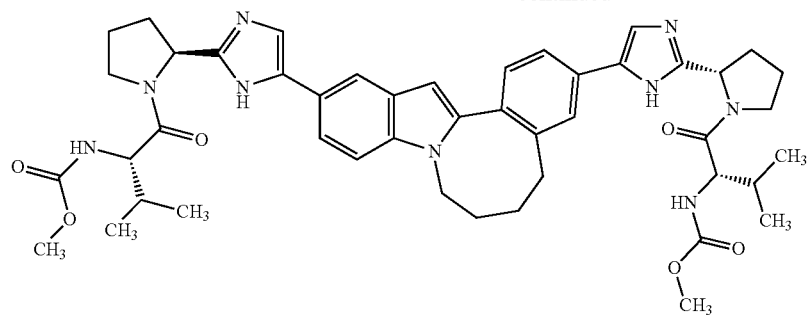
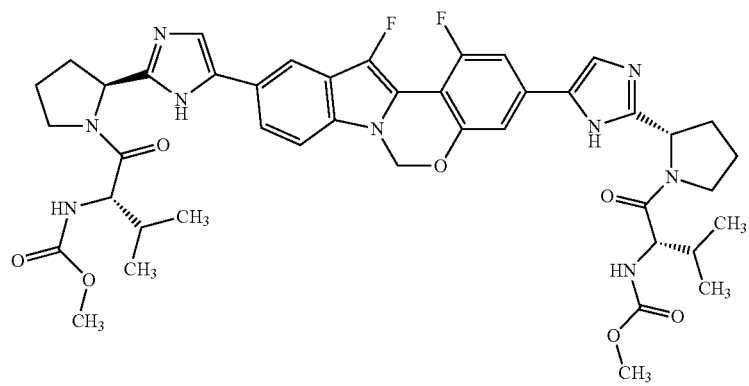
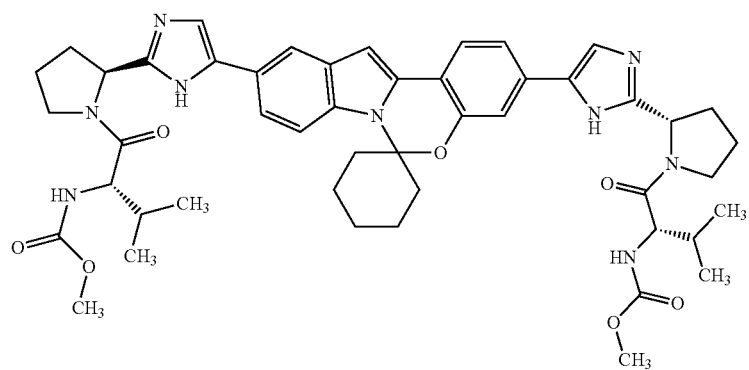
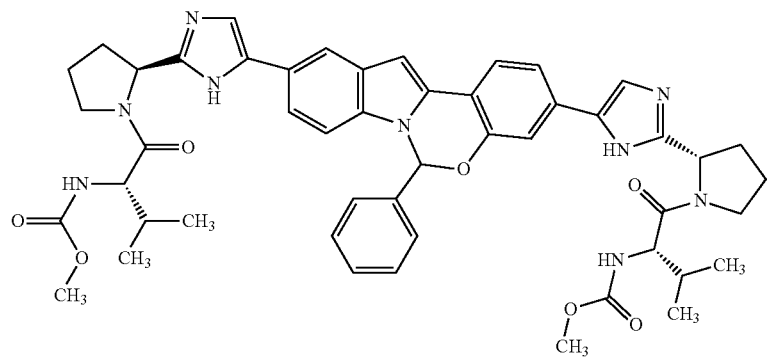

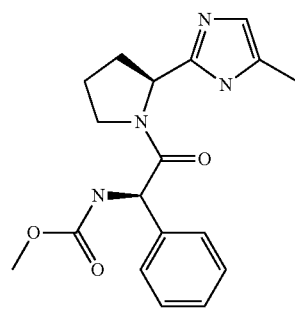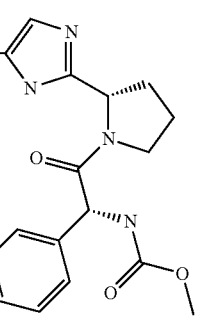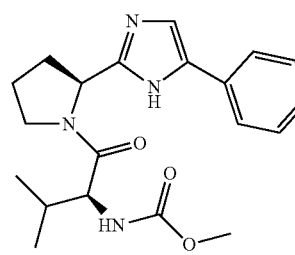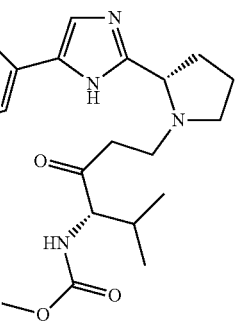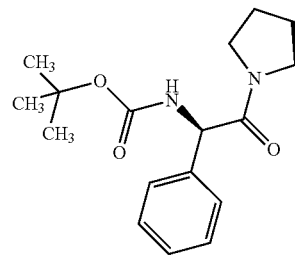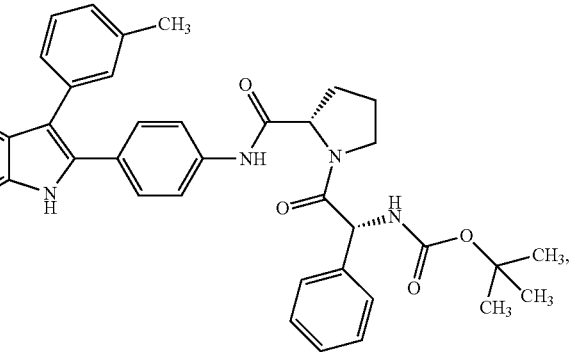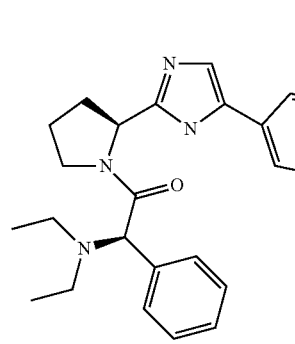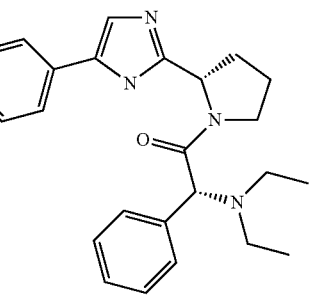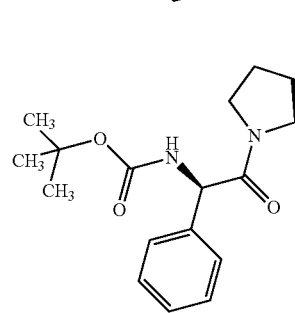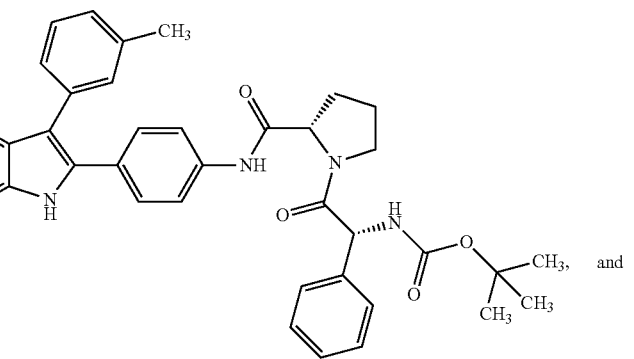

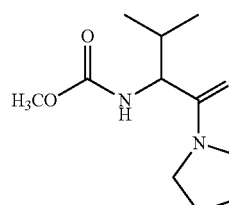

and pharmaceutically acceptable salts thereof.

HCV replicase inhibitors useful in the present compositions and methods include, but are not limited to, those disclosed in U.S. Patent Publication No. US20090081636.

The doses and dosage regimen of the other agents used in the combination therapies of the present invention for the treatment or prevention of HCV infection can be determined by the attending clinician, taking into consideration the approved doses and dosage regimen in the package insert; the age, sex and general health of the patient; and the type and severity of the viral infection or related disease or disorder. When administered in combination, the Cyclic Phosphonate Substituted Nucleoside Derivative(s) and the other agent(s) can be administered simultaneously (i.e., in the same composition or in separate compositions one right after the other) or sequentially. This particularly useful when the components of the combination are given on different dosing schedules, e.g., one component is administered once daily and another component is administered every six hours, or when the preferred pharmaceutical compositions are different, e.g., one is a tablet and one is a capsule. A kit comprising the separate dosage forms is therefore advantageous.

Generally, a total daily dosage of the at least one Cyclic Phosphonate Substituted Nucleoside Derivative(s) alone, or when administered as combination therapy, can range from about 1 to about 2500 mg per day, although variations will necessarily occur depending on the target of therapy, the patient and the route of administration. In one embodiment, the dosage is from about 10 to about 1000 mg/day, administered in a single dose or in 2-4 divided doses. In another embodiment, the dosage is from about 1 to about 500 mg/day, administered in a single dose or in 2-4 divided doses. In still another embodiment, the dosage is from about 1 to about 100 mg/day, administered in a single dose or in 2-4 divided doses. In yet another embodiment, the dosage is from about 1 to about 50 mg/day, administered in a single dose or in 2-4 divided doses. In another embodiment, the dosage is from about 500 to about 1500 mg/day, administered in a single dose or in 2-4 divided doses. In still another embodiment, the dosage is from about 500 to about 1000 mg/day, administered in a single dose or in 2-4 divided doses. In yet another embodiment, the dosage is from about 100 to about 500 mg/day, administered in a single dose or in 2-4 divided doses.

In a further embodiment, when the additional therapeutic agent is Ribavirin (commercially available as REBETOL ribavirin from Schering-Plough or COPEGUS ribavirin from Hoffmann-La Roche), this agent is administered at a daily dosage of from about 600 to about 1400 mg/day for at least 24 weeks.

Compositions and Administration

Due to their activity, the Cyclic Phosphonate Substituted Nucleoside Derivatives are useful in veterinary and human medicine. As described above, the Cyclic Phosphonate Substituted Nucleoside Derivatives are useful for treating or preventing HCV infection in a patient in need thereof.

When administered to a patient, the Cyclic Phosphonate Substituted Nucleoside Derivatives can be administered as a component of a composition that comprises a pharmaceutically acceptable carrier or vehicle. The present invention provides pharmaceutical compositions comprising an effective amount of at least one Cyclic Phosphonate Substituted Nucleoside Derivative and a pharmaceutically acceptable carrier. In the pharmaceutical compositions and methods of the present invention, the active ingredients will typically be administered in admixture with suitable carrier materials suitably selected with respect to the intended form of administration, i.e., oral tablets, capsules (either solid-filled, semi-solid filled or liquid filled), powders for constitution, oral gels, elixirs, dispersible granules, syrups, suspensions, and the like, and consistent with conventional pharmaceutical practices. For example, for oral administration in the form of tablets or capsules, the active drug component may be combined with any oral non-toxic pharmaceutically acceptable inert carrier, such as lactose, starch, sucrose, cellulose, magnesium stearate, dicalcium phosphate, calcium sulfate, talc, mannitol, ethyl alcohol (liquid forms) and the like. Solid form preparations include powders, tablets, dispersible granules, capsules, cachets and suppositories. Powders and tablets may be comprised of from about 0.5 to about 95 percent inventive composition. Tablets, powders, cachets and capsules can be used as solid dosage forms suitable for oral administration.

Moreover, when desired or needed, suitable binders, lubricants, disintegrating agents and coloring agents may also be incorporated in the mixture. Suitable binders include starch, gelatin, natural sugars, corn sweeteners, natural and synthetic gums such as acacia, sodium alginate, carboxymethylcellulose, polyethylene glycol and waxes. Among the lubricants there may be mentioned for use in these dosage forms, boric acid, sodium benzoate, sodium acetate, sodium chloride, and the like. Disintegrants include starch, methylcellulose, guar gum, and the like. Sweetening and flavoring agents and preservatives may also be included where appropriate.

Liquid form preparations include solutions, suspensions and emulsions and may include water or water-propylene glycol solutions for parenteral injection.

Liquid form preparations may also include solutions for intranasal administration.

Also included are solid form preparations which are intended to be converted, shortly before use, to liquid form preparations for either oral or parenteral administration. Such liquid forms include solutions, suspensions and emulsions.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Additionally, the compositions of the present invention may be formulated in sustained release form to provide the rate controlled release of any one or more of the components or active ingredients to optimize therapeutic effects, i.e., antiviral activity and the like. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

In one embodiment, the one or more Cyclic Phosphonate Substituted Nucleoside Derivatives are administered orally.

In another embodiment, the one or more Cyclic Phosphonate Substituted Nucleoside Derivatives are administered intravenously.

In one embodiment, a pharmaceutical preparation comprising at least one Cyclic Phosphonate Substituted Nucleoside Derivative is in unit dosage form. In such form, the preparation is subdivided into unit doses containing effective amounts of the active components.

Compositions can be prepared according to conventional mixing, granulating or coating methods, respectively, and the present compositions can contain, in one embodiment, from about 0.1% to about 99% of the Cyclic Phosphonate Substituted Nucleoside Derivative(s) by weight or volume. In various embodiments, the present compositions can contain, in one embodiment, from about 1% to about 70% or from about 5% to about 60% of the Cyclic Phosphonate Substituted Nucleoside Derivative(s) by weight or volume.

The quantity of Cyclic Phosphonate Substituted Nucleoside Derivative in a unit dose of preparation may be varied or adjusted from about 1 mg to about 2500 mg. In various embodiment, the quantity is from about 10 mg to about 1000 mg, 1 mg to about 500 mg, 1 mg to about 100 mg, and 1 mg to about 100 mg.

For convenience, the total daily dosage may be divided and administered in portions during the day if desired. In one embodiment, the daily dosage is administered in one portion. In another embodiment, the total daily dosage is administered in two divided doses over a 24 hour period. In another embodiment, the total daily dosage is administered in three divided doses over a 24 hour period. In still another embodiment, the total daily dosage is administered in four divided doses over a 24 hour period.

The amount and frequency of administration of the Cyclic Phosphonate Substituted Nucleoside Derivatives will be regulated according to the judgment of the attending clinician considering such factors as age, condition and size of the patient as well as severity of the symptoms being treated. Generally, a total daily dosage of the Cyclic Phosphonate Substituted Nucleoside Derivatives range from about 0.1 to about 2000 mg per day, although variations will necessarily occur depending on the target of therapy, the patient and the route of administration. In one embodiment, the dosage is from about 1 to about 200 mg/day, administered in a single dose or in 2-4 divided doses. In another embodiment, the dosage is from about 10 to about 2000 mg/day, administered in a single dose or in 2-4 divided doses. In another embodiment, the dosage is from about 100 to about 2000 mg/day, administered in a single dose or in 2-4 divided doses. In still another embodiment, the dosage is from about 500 to about 2000 mg/day, administered in a single dose or in 2-4 divided doses.

The compositions of the invention can further comprise one or more additional therapeutic agents, selected from those listed above herein. Accordingly, in one embodiment, the present invention provides compositions comprising: (i) at least one Cyclic Phosphonate Substituted Nucleoside Derivative or a pharmaceutically acceptable salt thereof; (ii) one or more additional therapeutic agents that are not a Cyclic Phosphonate Substituted Nucleoside Derivative; and (iii) a pharmaceutically acceptable carrier, wherein the amounts in the composition are together effective to treat HCV infection.

In one embodiment, the present invention provides compositions comprising a Compound of Formula (I) and a pharmaceutically acceptable carrier.

In another embodiment, the present invention provides compositions comprising a Compound of Formula (I), a pharmaceutically acceptable carrier, and a second therapeutic agent selected from the group consisting of HCV antiviral agents, immunomodulators, and anti-infective agents.

In another embodiment, the present invention provides compositions comprising a Compound of Formula (I), a pharmaceutically acceptable carrier, and wto additional therapeutic agents, each of which are independently selected from the group consisting of HCV antiviral agents, immunomodulators, and anti-infective agents.

Methods for Making the Compounds of Formula (I)

The Compounds of Formula (I) may be prepared from known or readily prepared starting materials, following methods known to one skilled in the art of organic synthesis. Methods useful for making the Compounds of Formula (I) are set forth in the Examples below and generalized in Schemes A and B below. Alternative synthetic pathways and analogous structures will be apparent to those skilled in the art of organic synthesis.

Scheme A shows a method useful for making nucleoside compounds of formulas F and G, which correspond to the Compounds of Formula (I), wherein X is O; $R^1$ is methyl, $R^2$ is —$NH_2$ and B is:

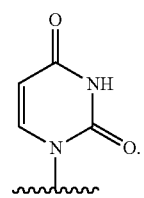 [SMILES: *n1ccc(=O)[nH]c1=O]

Scheme A

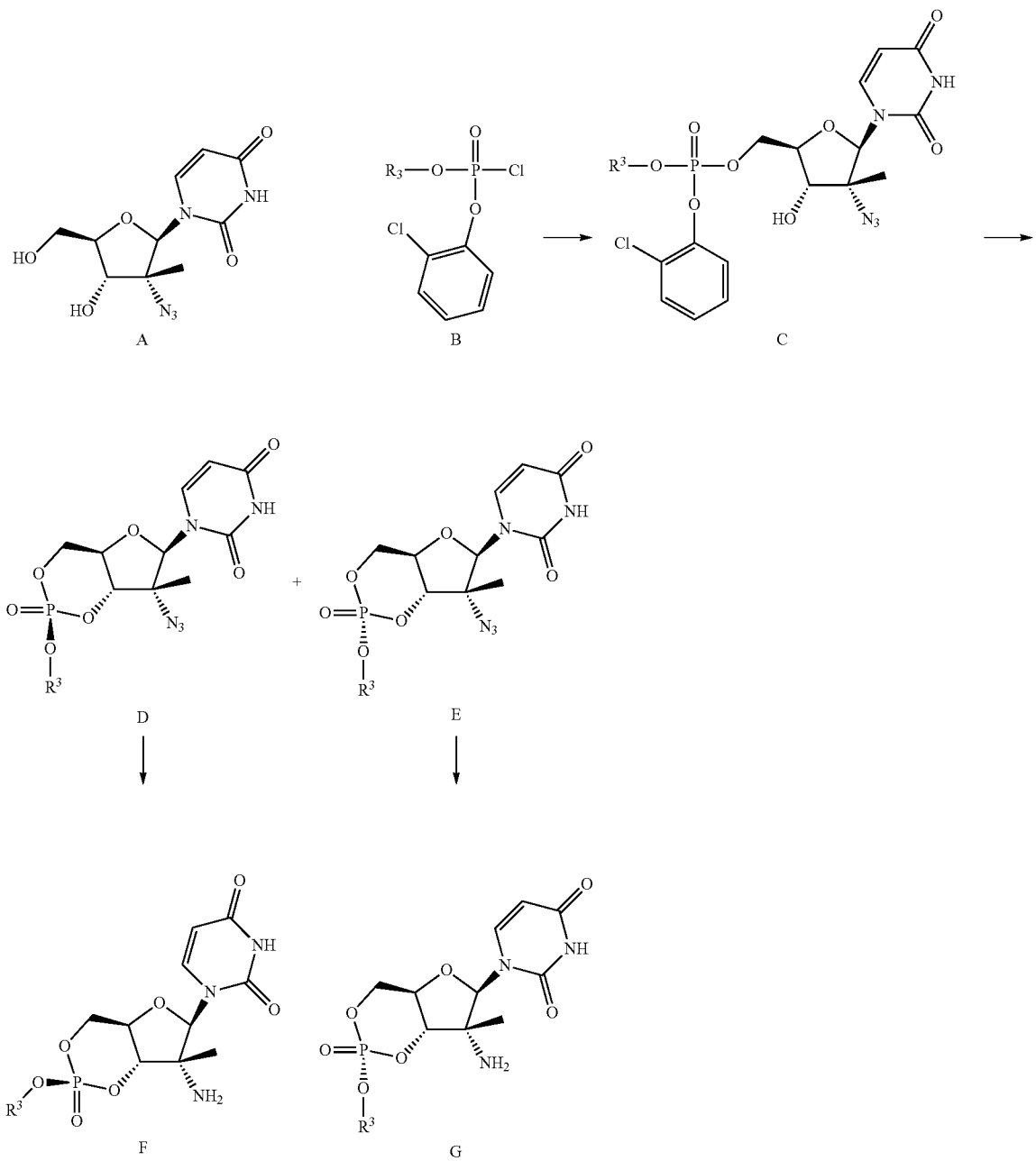

Wherein R³ is as defined above for the Compounds of Formula (I).

A 2'-Azido uridine nucleoside compound of formula A can be reacted with a compound of formula B in the presence of a non-nucleophilic base, such as N-methylimidazole, to provide compounds of formula C. Compounds of formula C can then cyclized in the presence of an alkali metal alkoxide base, such as potassium t-butoxide, to provide the cyclic phosphonate isomers of formulas D and E. Subsequent reduction of the azido moiety of D and E, using for example, catalytic hydrogenation, provides the corresponding 2'-amino compounds of formulas F and G, respectively.

Scheme B shows an alternate method useful for making nucleoside compounds of formulas F and G, which correspond to the Compounds of Formula (I), wherein X is O; R¹ is methyl, R² is —NH₂ and B is:

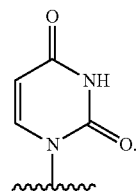 [SMILES: *n1ccc(=O)[nH]c1=O]

Scheme B

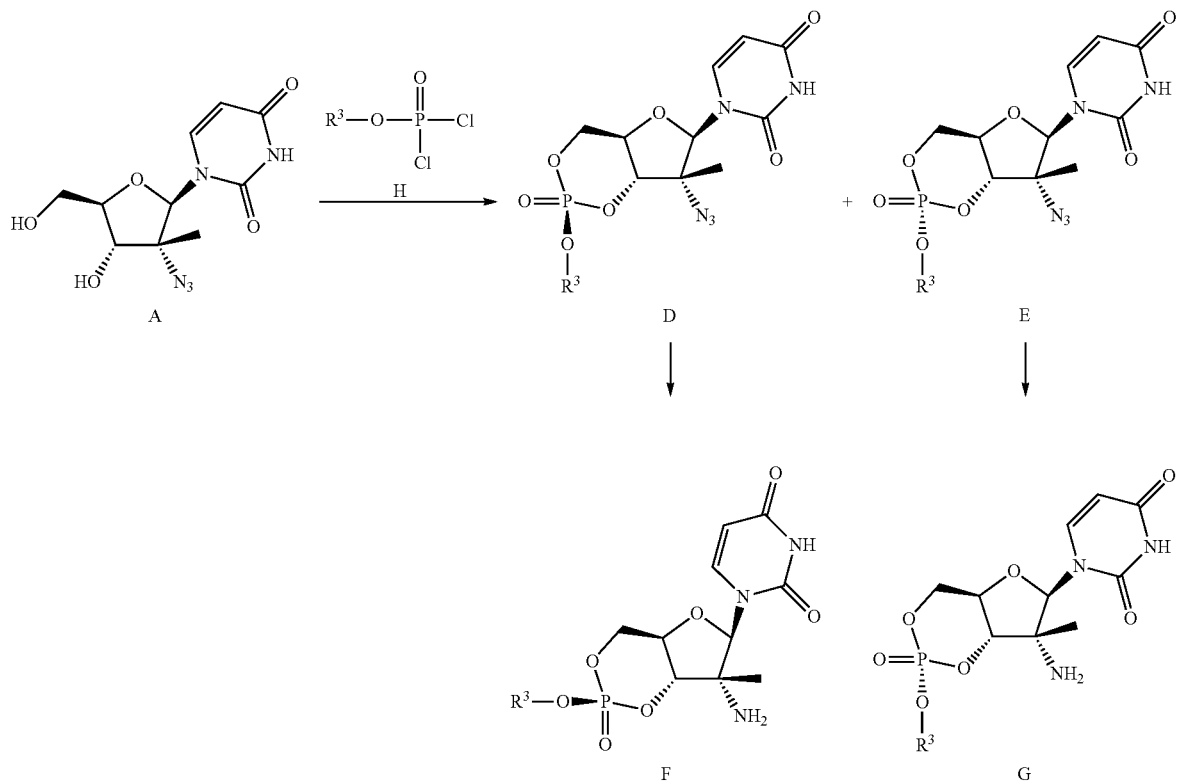

Wherein $R^3$ is as defined above for the Compounds of Formula (I).

A 2'-Azido uridine nucleoside compounds of formula A can be reacted with a compound of formula H, in the presence of a non-nucleophilic base, such as triethylamine, to provide compounds of formula D and E. Subsequent reduction of the azido moiety of D and E, using for example, catalytic hydrogenation, provides the corresponding 2'-amino compounds of formulas F and G, respectively.

One skilled in the art of organic synthesis will recognize that the synthesis of compounds with multiple reactive functional groups, such as —OH and $NH_2$, may require protection of certain functional groups (i.e., derivatization for the purpose of chemical compatibility with a particular reaction condition). Suitable protecting groups for the various functional groups of these compounds and methods for their installation and removal are well known in the art of organic chemistry. A summary of many of these methods can be found in, T. W. Greene et al, *Protective Groups in Organic Synthesis* (1991), Wiley, New York.

One skilled in the art of organic synthesis will also recognize that one route for the synthesis of the Compounds of Formula (I) may be more desirable depending on the choice of appendage substituents. Additionally, one skilled in the relevant art will recognize that in some cases the order of reactions may differ from that presented herein to avoid functional group incompatibilities and thus adjust the synthetic route accordingly.

The starting materials used and the intermediates prepared using the methods set forth in Schemes A and B may be isolated and purified if desired using conventional techniques, including but not limited to filtration, distillation, crystallization, chromatography and alike. Such materials can be characterized using conventional means, including physical constants and spectral data.

Non-limiting examples of the Compounds of Formula (I) include compounds 1-7 as set forth in the Examples below, and pharmaceutically acceptable salts thereof.

EXAMPLES

General Methods

Solvents, reagents, and intermediates that are commercially available were used as received. Reagents and intermediates that are not commercially available were prepared in the manner as described below. $^1$H NMR spectra were obtained on a Varian VNMR System 400 (400 MHz) and are reported as ppm downfield from $Me_4Si$ with number of protons, multiplicities, and coupling constants in Hertz indicated parenthetically. Where LC/MS data are presented, analyses was performed using an Agilent 6110A MSD or an Applied Biosystems API-100 mass spectrometer and Shimadzu SCL-10A LC column: Altech platinum C18, 3 micron, 33 mm×7 mm ID; gradient flow: 0 minutes—10% $CH_3CN$, 5 minutes—95% $CH_3CN$, 5-7 minutes—95% $CH_3CN$, 7 minutes—stop. The parent ion is given. Flash chromatography on silica gel was performed using pre-packed normal phase silica from Isco, Biotage, Inc. or bulk silica from Fisher Scientific. Unless otherwise indicated, flash chromatography on silica gel was performed using a gradient elution of hexanes/ethyl acetate, from 100% hexanes to 100% ethyl acetate.

Example 1

Preparation of Intermediate Compound 1a

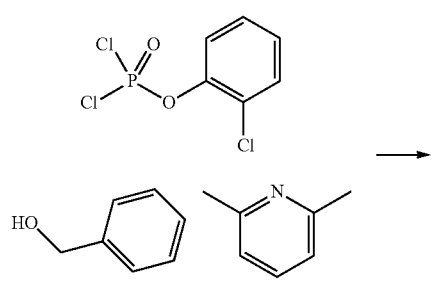

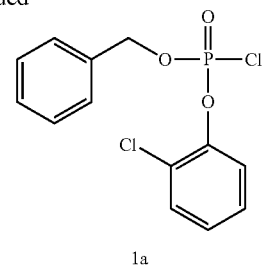

To a solution of 2-chlorophenyl phosphorodichloridate (3.29 mL, 20.37 mmol) in THF (30 mL) stirred at 0° C. was added benzyl alcohol (2.118 mL, 20.37 mmol) followed by dropwise addition of 2,6-lutidine (2.373 mL, 20.37 mmol). The cold bath was removed and the reaction mixture allowed to stir overnight at room temperature. Next day, the reaction mixture was filtered and washed with 100 mL of THF. The filtrate was concentrated to provide the crude desired product Int-1a (6.4 g, 99%). $^1$H-NMR (CDCl$_3$, 500 MHz, ppm): δ 7.38-7.57 (m, 9H), 5.40-5.43 (m, 2H).

Example 2

Preparation of Compounds 1 and 2

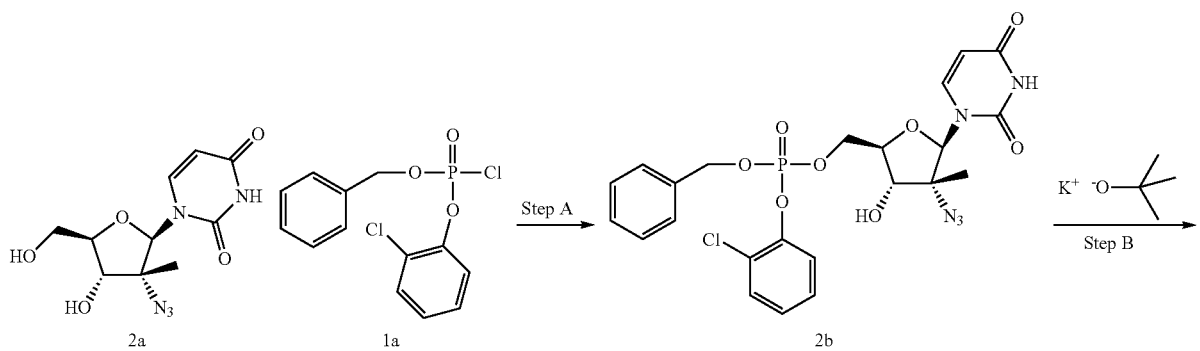

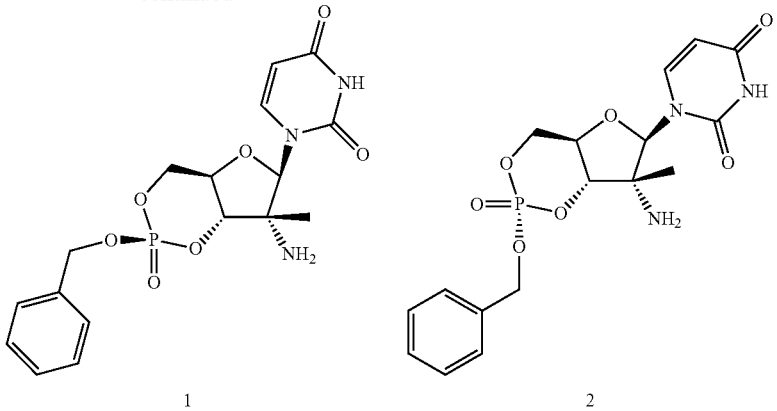

Step A: Synthesis of Intermediate 2b.

To a solution of 2a (500 mg, 1.765 mmol, made using the method described in International Application No. WO 2012/142085) in THF (20 mL) was added 1-methylimidazole (1.15 g, 14.12 mmol) followed by dropwise of 1a (2.23 g, 7.06 mmol) at 0° C. After 1 hour, the reaction was quenched with saturated ammonium chloride and extracted with ethyl acetate. The organic layer was washed with water, brine, dried over $Na_2SO_4$, filtered, and concentrated in vacuo. The residue was purified using silica gel flash column chromatography (0 to 20% $CH_3OH/CH_2Cl_2$) to provide the product 2b (514 mg, 52%). (ES, m/z): 564.25 [M+H]$^+$, $^1$H-NMR (CD$_3$OD, 500 MHz, ppm): δ 7.50-7.52 (m, 2H), 7.22-7.49 (m, 8H), 5.80 (s, 1H), 5.50-5.52 (m, 1H), 5.26-5.30 (m, 2H), 4.58-4.62 (m, 1H), 4.45-4.50 (m, 1H), 4.06-4.11 (m, 1H), 3.97-3.98 (m, 1H), 1.33 (s, 3H).

Step B: Synthesis of Intermediates 2c and 2d.

To a solution of 2b (500 mg, 0.887 mmol) in THF (100 mL) was cooled at 0° C. for 30 minutes then potassium tert-butoxide (219 mg, 1.95 mmol) was added. The reaction was stirred for 20 minutes and quenched with acetic acid (0.406 mL, 7.09 mmol). The reaction mixture was filtered and the filtrate was concentrated in vacuo. The residue was purified using preparative TLC using 100% EtOAc to provide compounds 2c (115 mg, 29%) and 2d (102 mg, 26%).

Compound 2c: (ES, m/z): 436.24 [M+H]$^+$, $^1$H-NMR (CD$_3$OD, 500 MHz, ppm): δ 7.36-7.53 (m, 6H), 6.00 (s, 1H), 5.76 (d, J=8.0 Hz, 1H), 5.20 (d, J=10.9 Hz, 2H), 4.64-4.71 (m, 1H), 4.54-4.58 (m, 1H), 4.22-4.26 (m, 1H), 4.09-4.11 (m, 1H), 1.21 (s, 3H).

Compound 2d: (ES, m/z): 436.26 [M+H]$^+$, $^1$H-NMR (CD$_3$OD, 500 MHz, ppm): δ 7.60 (d, J=8.1 Hz, 1H), 7.33-7.45 (m, 5H), 6.06 (s, 1H), 5.78 (d, J=8.0 Hz, 1H), 5.19 (d, J=9.0 Hz, 2H), 4.60-4.68 (m, 3H), 4.41-4.46 (m, 1H), 1.45 (s, 3H).

Step C: Synthesis of Compound 1

To a solution of 2c (2.0 g, 4.59 mmol) in THF (39 mL) and water (7.80 mL) was added trimethylphosphine (9.19 mL, 9.19 mmol) at room temperature. The reaction mixture was stirred for 90 minutes then removed solvent to dryness. The residue was treated with 45 mL of CH$_3$CN with 0.05% TFA (v/v) and 5 mL of H$_2$O with 0.05% TFA (v/v), both from commercial source, stirred at 60° C. for 40 minutes. The reaction was quenched with 30 mL saturated sodium bicarbonate, pH~9 and diluted with ethyl acetate. The layers were separated. The aqueous layer was extracted with EtOAc. The organic layers were combined and washed with brine, dried with Na$_2$SO$_4$, filtered and concentrated. The residue was purified using silica gel flash column chromatography (0 to 20% CH$_3$OH/CH$_2$Cl$_2$) to provide the product 1 (1.36 g, 72%). (ES, m/z): 410.36 [M+H]$^+$, $^1$H-NMR (CD$_3$OD, 500 MHz, ppm): δ 7.48-7.53 (m, 3H), 7.36-7.43 (m, 3H), 5.96 (s, 1H), 5.72 (d, J=7.7 Hz, 1H), 5.18 (d, J=10.4 Hz, 2H), 4.64-4.68 (m, 1H), 4.53-4.56 (m, 1H), 4.32-4.39 (m, 1H), 3.96-3.98 (m, 1H), 0.97 (s, 3H).

Step D: Synthesis of Compound 2

Compound 2 was made using the method described in Step C immediately above. (ES, m/z): 410.16 [M+H]$^+$, $^1$H-NMR (CD$_3$OD, 500 MHz, ppm): δ 7.63 (d, J=7.9, 1H), 7.36-7.46 (m, 5H), 6.02 (s, 1H), 5.74 (d, J=7.7 Hz, 1H), 5.20 (d, J=9.2 Hz, 2H), 4.51-4.66 (m, 3H), 4.39-4.40 (m, 1H), 1.18 (s, 3H).

Example 3

Preparation of Compounds 3 and 4

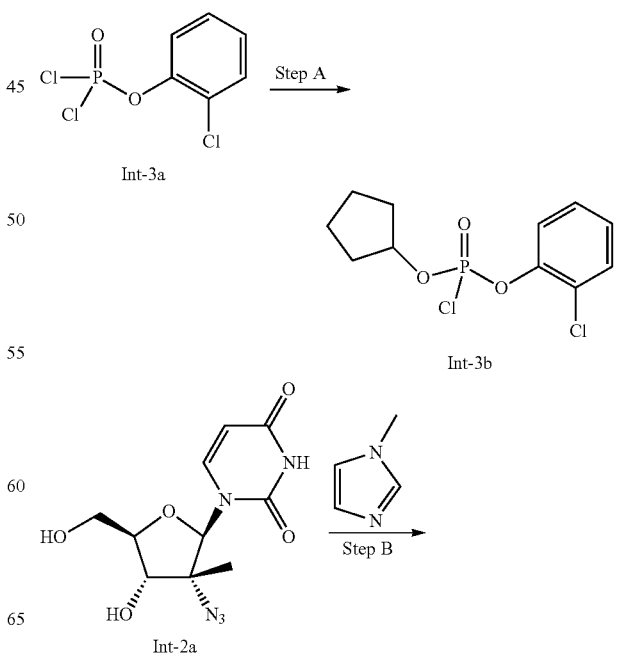

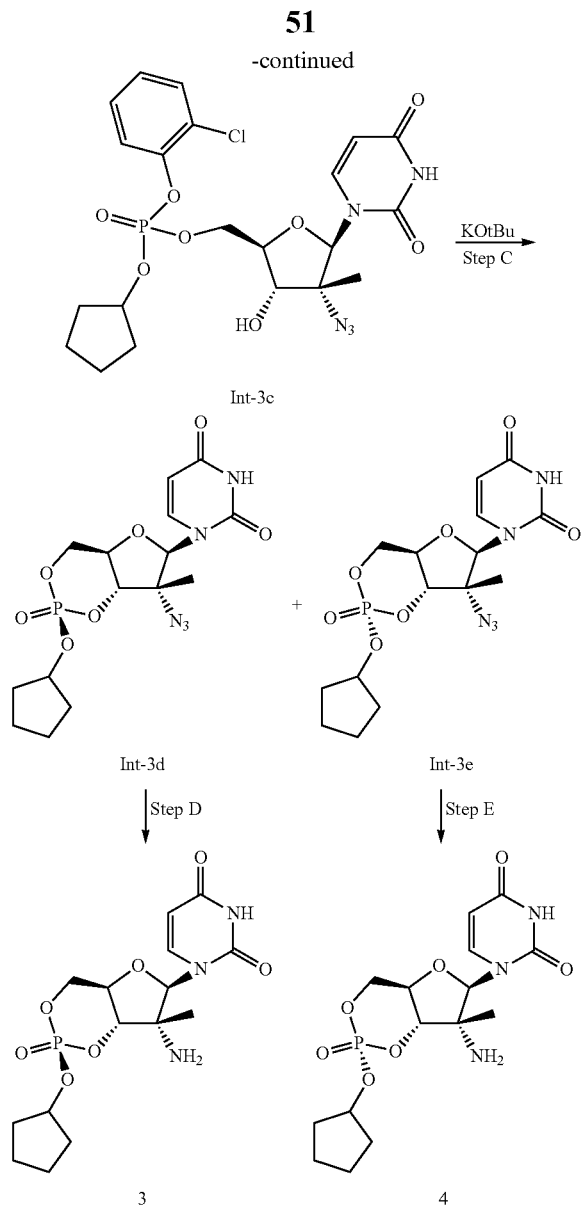

Step A—Synthesis of Compound Int-3b

A stirred solution of compound Int-3a (10.0 g, 40.7 mmol) in 40 mL of anhydrous THF was cooled in ice bath to 0° C., cyclopentanol (3.51 g, 40.7 mmol) was added dropwise, followed by dropwise addition of 2,6-lutidine (4.37 g, 40.7 mmol). The reaction was allowed to warm to room temperature and stirred for 3 hours with white solid precipitated out. Filtered the reaction mixture, washed the white solid with THF. The filtrate was concentrated in vacuo to offer a clear oil that was purified using silica gel flash chromatography (0-40% EtOAc/Hexanes) to provide product Int-3b (6.38 g, 53%). $^1$H NMR δ (ppm)(CHCl$_3$-d): 1.09-1.16 (1H, m), 1.47-1.55 (1H, m), 1.64-1.72 (2H, m), 1.72-1.82 (2H, m), 1.85-1.95 (2H, m), 5.15-5.16 (1H, m), 7.03 (1H, t, J=7.78 Hz), 7.12-7.13 (1H, m), 7.29 (1H, d, J=8.03 Hz), 7.36 (1H, d J=8.28 Hz).

Step B—Synthesis of Compound Int-3c

Compound Int-2a (1 g, 3.53 mmol) was dissolved in THF (10 mL) in an ice bath, then followed by the addition of NMI (2.9 g, 35.3 mmol). The mixture was stirred for 15 minutes till the clear reaction solution was formed. The phosphorous reagent Int-3b (1.04 g, 3.52 mmol) in 3 mL of THF was added dropwise to the above reaction solution. The reaction mixture was allowed to warm up to room temperature and stirred for 1 hour. LC-MS showed that reaction gave one major new product peak and starting material (ratio about 1:1). The reaction solution was cooled in ice bath and then added NMI (0.15 g, 1.76 mmol). After stirring for 15 minutes, Int-3b (0.5 g, 1.76 mmol) was added dropwise. Remove ice bath and 15 minutes later LCMS showed that the reaction was complete ([M+H]=542.4). The reaction was quenched with water and extracted with ethyl acetate. The organic layer was washed with saturated ammonium chloride and then washed with 0.5N HCl (aq. pH=3), water, and then brine. The organic layer was dried over sodium sulfate, filtered and concentrated in vacuo to provide a crude product Int-3c (1.92 g) which was not purified and used directly in next step.

Step C—Synthesis of Int-3d and Int-3e

Compound Int-3c (1.92 g, 3.54 mml) was dissolved in THF (10 mL) and cooled in an ice bath. tBuOK (0.795 g, 7.09 mmol) was added to the reaction solution in one portion. The reaction was allowed to stir at room temperature for 30 minutes. LC-MS indicated most starting material was consumed and two major product peaks were formed. The reaction was cooled down in an ice bath, then quenched with saturated ammonium chloride. The reaction solution was extracted with EtOAc (400 mL), washed with water, and brine. The organic layer was dried over Na$_2$SO$_4$, filtered and concentrated in vacuo. The resulting residue was purified using flash column chromatography on silica gel (Hexane:EtOAc 0-100%) to provide Int-3d (less polar, 260 mg, 17% yield, [M+H]=414.3) and Int-3e (more polar, 317 mg, 21% yield, [M+H]=414.3).

Step D—Synthesis of 3

To isomer Int-3d (260 mg, 0.629 mmol) in MeOH (10 mL) was added 10% w/w Pd/C (26 mg, 10% wt), affixed a H$_2$ balloon, stirred for 30 minutes. LCMS indicated reaction incomplete. After 1 hour, added Pd/C (13 mg) and 0.5 ml MeOH, put back H2 balloon for 0.5 hours. LCMS indicated reaction complete. The reaction mixture was filtered through celite and the filtrate was concentrated under reduced pressure. The resulting residue was purified using flash column chromatography on silica gel (10% MeOH/CH$_2$Cl$_2$). The fractions containing the desire product molecule weight was combined and concentrated and the resulting residue was add MeOH (10 mL) and heated to 50° C. for 36 hours. The solvent was removed to provide the desired compound 3 (206 mg, 85% yield). $^1$H NMR δ (ppm)(CH$_3$OH-d$_4$): 1.18 (3 H, s), 1.64-1.66 (1 H, m), 1.72-1.77 (1H, m), 1.82-1.94 (6 H, m), 4.32 (1 H, d, J=9.52 Hz), 4.48 (1 H, br s), 4.60 (1 H, br s), 4.62-4.75 (1 H, m), 4.96-5.04 (1 H, m), 5.73 (1 H, d, J=8.06 Hz), 6.01 (1 H, s), 7.60 (1 H, d, J=8.06 Hz).

Step E—Synthesis of 4

To Int-3e (317 mg, 0.767 mmol) in MeOH (10 mL) was added 10% w/w Pd/C (32 mg, 10% wt), affixed a H$_2$ balloon, stirred for 1 hour. LCMS indicated the reaction complete. The reaction mixture was filtered through celite and the filtrate was concentrated under reduced pressure. The resulting residue was purified using flash column chromatography on silica gel (10% MeOH/CH$_2$Cl$_2$). The fractions containing the desire product molecule weight was combined and concentrated and the resulting residue was add MeOH (10 mL) and heated to 50° C. for 36 hours. The solvent was removed in vacuo to provide the desired compound 4 (225 mg, 76% yield). $^1$H NMR δ (ppm)(CH$_3$OH-d$_4$): 1.18 (3 H, s), 1.58-1.70 (1 H, m), 1.72-1.82 (1 H, m), 1.82-1.97 (6H, m), 4.32 (1 H, d, J=9.70 Hz), 4.42-4.50 (1 H, m), 4.54-4.62

(1 H, m), 4.66-4.72 (1 H, m), 4.98-5.02 (1 H, m), 5.72 (1 H, d, J=8.13 Hz), 6.00 (1 H, s), 7.66 (1 H, d, J=8.12 Hz).

Example 4

Preparation of Compounds 5 and 6

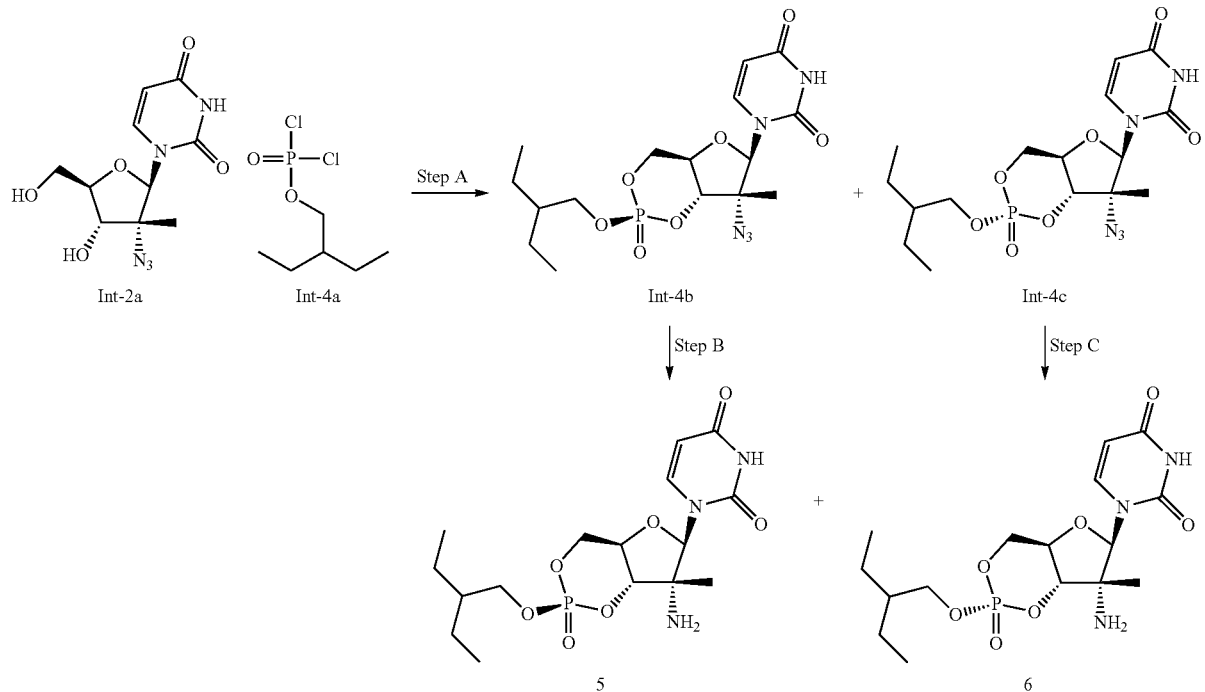

Step A—Synthesis of Compounds Int-4b and Int-4c

Into a 100-mL round-bottom flask purged and maintained with an inert atmosphere of argon, was placed a solution of compound Int-2a (1 g, 3.53 mmol) in DCM/1,4-dioxane (14/6 mL). The resulting solution was stirred for 30 minutes at room temperature, then triethylamine (1.5 g, 14.82 mmol) was added dropwise. This was followed by the addition of (2-ethylbutoxy)phosphonoyl dichloride Int-4a (1.09 g, 4.98 mmol, using the method described in Example 1 above) dropwise with stirring at −20° C. in 15 minutes. After the resulting solution was stirred for an additional 30 minutes while the temperature was maintained at −15° C. in a liquid nitrogen bath, N-methyl imidazole (0.695 g, 2.40 equivalents) was added dropwise with stirring at −15° C. in 20 minutes. The resulting solution was stirred overnight at room temperature, and then it was diluted with 100 mL of DCM, washed with 3×30 mL of H$_2$O, dried over anhydrous sodium sulfate and concentrated under vacuum. The residue was applied onto a silica gel column with ethyl acetate/petroleum ether (1:1) to provide 150 mg (10%) of compound Int-4b as a white solid and 150 mg (10%) of compound Int-4c as a white solid.

Step B—Synthesis of Compound 5

Into a 50-mL round-bottom flask purged and maintained with an inert atmosphere of argon, was placed a solution of compound Int-4b (150 mg, 0.35 mmol) in ethanol (6 ml), Pd(OH)$_2$/C (50 mg). After the resulting solution was stirred for 2 hours at room temperature under hydrogen, the solids were filtered out and the filtrate was concentrated under vacuum. The crude product (120 mg) was purified using Prep-HPLC with the following conditions (1#-Pre-HPLC-011(Waters)): Column, XBridge Shield RP18 OBD Column, 5 um, 19*150 mm; mobile phase, Water with 10 mmol NH$_4$HCO$_3$ and CH$_3$CN (5.0% CH$_3$CN up to 80.0% in 12 min); Detector, UV 254 & 220 nm. This resulted in 75.9 mg (54%) of compound 5 as a white solid. LC-MS: (ES, m/z): 404 [M+H]$^+$, H-NMR: (300 MHz, CD$_3$OD, ppm): δ 7.60-7.75 (m, 1H), 6.02 (s, 1H), 5.76 (d, J=8.4 Hz, 1H), 4.50-4.80 (m, 2H), 4.35-4.50 (m, 1H), 4.09-4.14 (m, 3H), 1.61-1.63 (m, 1H), 1.42-1.52 (m, 4H), 1.09 (s, 3H), 0.94-0.99 (m, 6H). P-NMR: (162 MHz, CD$_3$OD, ppm): δ −5.416

Step C—Synthesis of Compound 6

Into a 50-mL round-bottom flask purged and maintained with an inert atmosphere of argon, was placed a solution of compound Int-4c (150 mg, 0.35 mmol) in ethanol (6 ml), Pd(OH)$_2$/C (50 mg). The resulting solution was stirred for 6 hours at room temperature under hydrogen and then the solids were filtered out and the filtrate was concentrated under vacuum. The crude product (100 mg) was purified using Prep-HPLC with the following conditions (1#-Pre-HPLC-011(Waters)): Column, SunFire Prep C18 OBD Column, 5 um, 19*150 mm; mobile phase, Water with 10 mmol of NH$_4$HCO$_3$ and CH$_3$CN (5.0% CH$_3$CN up to 75.0% in 12 min); Detector, UV 254 & 220 nm. This resulted in 47.0 mg (33%) of compound 6 as a white solid. LC-MS: (ES, m/z): 404, [M+H]$^+$ H-NMR:(300 MHz, CD$_3$OD, ppm): δ 7.65-7.67 (m, 1H), 6.04 (s, 1H), 5.76 (d, J=7.8 Hz, 1H), 4.49-4.76 (m, 4H), 4.36-4.39 (t, J=5.1 Hz, 2H), 1.56-1.61 (m, 1H), 1.41-1.48 (m, 4H), 1.23 (s, 3H), 0.90-1.00 (m, 6H), P-NMR: (162 MHz, CD$_3$OD, ppm): δ-3.567.

Example 5

Preparation of Compound 7

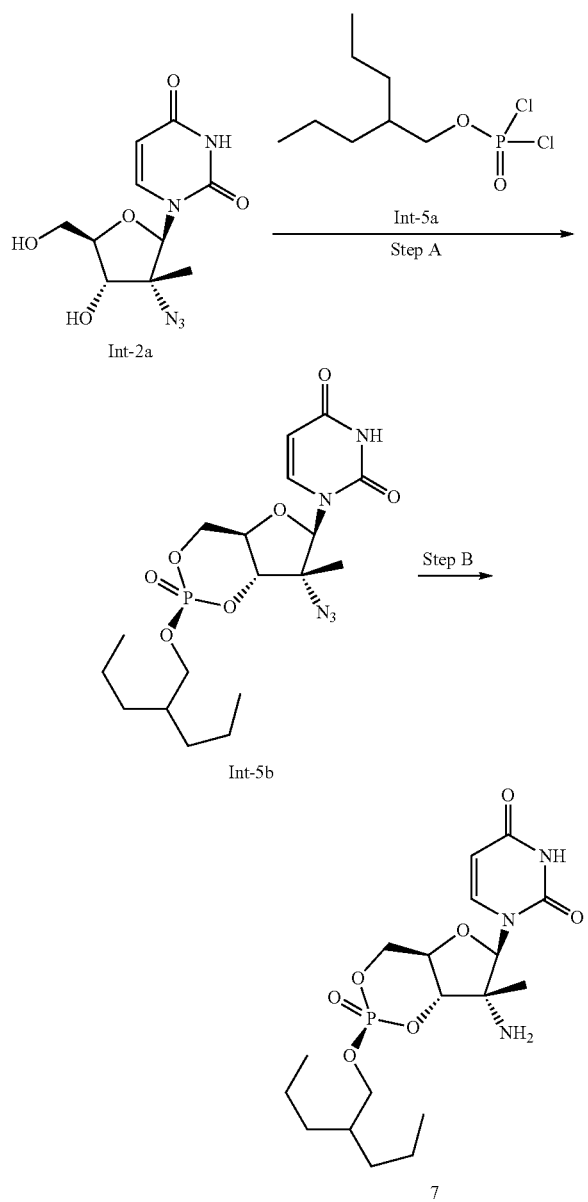

Step A—Synthesis of Compound Int-5b

Into a 50-mL round-bottom flask, was placed a solution of compound Int-2a (400 mg, 1.41 mmol) in DCM (40 mL). The resulted mixture was stirred at room temperature for 30 minutes, then triethylamine (0.8 mL) was added dropwise with stirring at −15° C. To this was added Int-5a (523 mg, 2.12 mmol, made using the method described in Example 1 above) dropwise with stirring at −15° C. in 30 minutes. The resulted mixture was allowed to reaction with stirring at −15° C. for 60 minutes. To the mixture was added 1-methyl-1H-imidazole (278 mg) dropwise with stirring at −15° C. in 30 minutes. After the resulting solution was stirred overnight at room temperature, the resulting mixture was concentrated under vacuum. The residue prepared by Preparative-TLC (dichloromethane/methanol 15:1) to provide 60 mg (7%) of Int-5b as colorless oil which was used for the next reaction directly.

Step B—Synthesis of Compound 7

Into a 25-mL round-bottom flask, was placed a solution of compound Int-5b (60 mg, 0.13 mmol) in ethanol (5 mL). This was followed by the addition of $Pd(OH)_2/C$ (12 mg, 0.09 mmol). After the resulting solution was stirred for 3 hours at room temperature under hydrogen, the solids were filtered out and the filtrate was concentrated in vacuo. The crude product (80 mg) was purified using Prep-HPLC with the following conditions (1#-Pre-HPLC-011(Waters)): Column, SunFire Prep C18, 19*150 mm Sum; mobile phase, water and acetonitrile (20.0% acetonitrile up to 79.0% in 8 min, up to 100.0% in 1 min, down to 20.0% in 1 min); Detector, UV 254 & 220 nm to provide 20 mg (35%) of compound 7 as a white solid. LCMS: 432 [M+H]+, H-NMR: (300 MHz, $CD_3OD$, ppm): 7.55 (d, J=7.2 Hz, 1H), 5.95(s, 1H), 5.64(d, J=7.2 Hz, 1H), 4.19-4.87 (m, 3H), 3.92-4.01 (m, 3H), 1.62-1.70(m, 1H), 1.10-1.32 (m, 11H), 0.70-0.90 (m, 6H). P-NMR: (300 MHz, $CD_3OD$, ppm): -5.435(s).

Example 6

Preparation of Compound 8 and 9

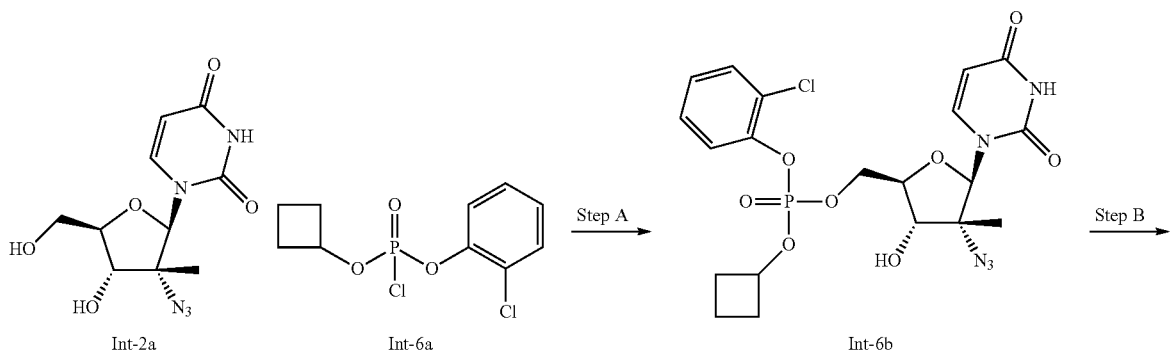

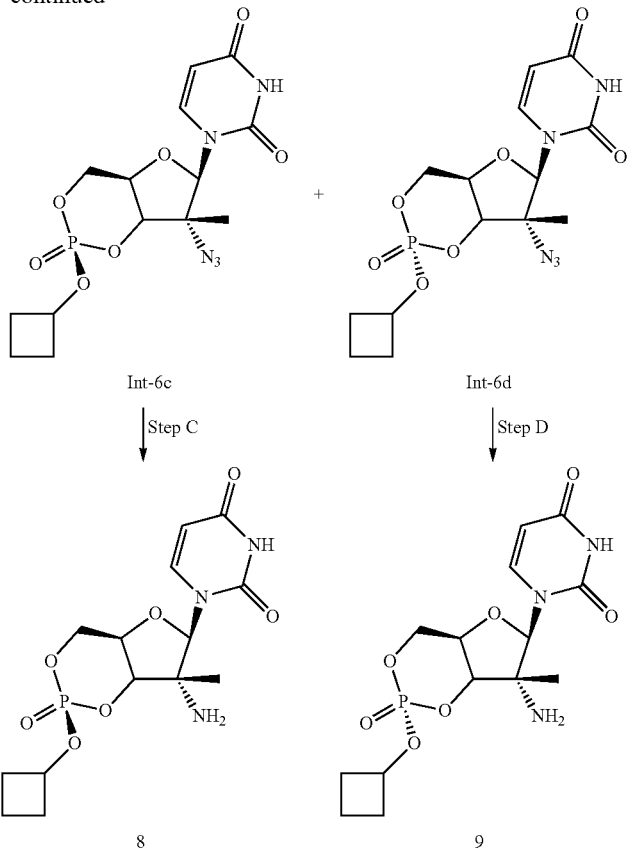

Step A: Synthesis of Int-6b

To a stirred solution of compound Int-2a (1.00 g, 3.53 mmol) in 3 ml NMP, was added 12 ml THF, then followed by addition of 1-methyl-1H-imidazole(NMI) (2.90 g, 35.3 mmol) under 0° C. ice bath. The reaction was stirred at 0° C. for 15 minutes then to the clear solution was added compound Int-6a (1.49 g, 5.30 mmol, using the method described in Example 1 above) dissolved in THF (2 mL) dropwise. The reaction was allowed to warm up to room temperature and stirred for 3 hours. LC-MS showed mainly product. Quenched the reaction with $H_2O$ (20 ml), diluted with EtOAc (400 ml). The organic layer was washed with saturated $NH_4Cl$ (aq. pH=9, 50 ml×2), then washed with 0.5N HCl (aq. pH=3, 20 ml), then washed with brine, and dried over $Na_2SO_4$, filtered and concentrated in vacuo. The residue was purified using silica gel flash column chromatography (0-100% EtOAc/Hexanes) to provide the product Int-6b (1.51 g, 81%). $^1$H NMR δ (ppm)($CH_3OH$-$d_4$): 1.36 (3 H, d, J=8.29 Hz), 1.60 (1H, d, J=7.40 Hz), 1.81 (1 H, br, s), 2.26-2.24 (2 H, m), 2.39-2.36 (2 H, br, s), 4.02 (1 H, s), 4.12-4.10 (1 H, m), 4.48 (1 H, t, J=5.55 Hz), 4.62 (1 H, m), 4.96-4.94 (1 H, m), 5.64 (1 H, t, J=8.66 Hz), 5.83 (1 H, s), 7.25-7.23 (1 H, m), 7.33 (1 H, t, J=7.64 Hz), 7.43 (1 H, d, J=8.29 Hz), 7.52 (1 H, d, J=7.46 Hz), 7.61 (1 H, dd, J=13.40, 8.13 Hz).

Step B: Synthesis of Compounds Int-6c and Int-6d

A stirred solution of compound Int-6d (1.51 g, 2.86 mmol) in THF (18 ml) was added tBuOK (0.64 g, 5.72 mmol) at 0° C. ice bath. Allowed the reaction to warm up to room temperature and stir for 8 hours. LC-MS showed mainly product as two isomers. Cooled the reaction down to 0° C. with an ice bath, quenched with saturated $NH_4Cl$, added 1N HCl to adjust to pH7. Extracted with EtOAc (400 ml), then washed the organic layer with $H_2O$ and brine, and dried over $Na_2SO_4$, filtered and concentrated in vacuo. The residue was purified using silica gel flash column chromatography (0-100% EtOAc/Hexanes) to provide the products Int-6c and Int-6d respectively as pure isomers. (Int-6c: 297.5 mg, 26.0%; Int-6d: 226.8 mg, 19.8%). Int-6c: $^1$H NMR δ (ppm) ($CH_3OH$-$d_4$): 1.48 (3 H, s), 1.64-1.61 (1 H, m), 1.84 (1 H, q, J=10.04 Hz), 2.39-2.31 (4 H, m), 4.31-4.29 (2 H, m), 4.58 (1 H, d, J=9.81 Hz), 4.70-4.65 (1 H, m), 4.85 (1 H, s), 5.78 (1 H, d, J=8.13 Hz), 6.07 (1 H, s), 7.69 (1 H, d, J=8.15 Hz).

Int-6d: $^1$H NMR δ (ppm)($CH_3OH$-$d_4$): 1.48 (3 H, s), 1.62-1.61 (1 H, m), 1.83 (1 H, q, J=10.50 Hz), 2.29-2.25 (2 H, m), 2.41 (2 H, t, J=9.06 Hz), 4.43 (1 H, t, J=7.85 Hz), 4.56 (1 H, d, J=9.74 Hz), 4.64-4.61 (1 H, m), 4.74 (1 H, dd, J=14.68, 6.99 Hz), 4.85 (1 H, s), 5.77 (1 H, d, J=8.17 Hz), 6.08 (1 H, s), 7.63 (1 H, d, J=8.16 Hz).

Step C: Synthesis of Compound 8

A stirred solution of compound Int-6c (297.5 mg, 0.75 mmol) in MeOH (8 ml), was added Pd/C (10% w/w, 30 mg, 10% wt), affixed a $H_2$ balloon, stirred at room temperature for 1 hour. Filtered the reaction mixture through a Celite plug and washed with MeOH (20 ml). The filtrate was concentrated in vacuo. The residue was purified using silica gel flash column chromatography (0-10% MeOH/$CH_2Cl_2$) to provide the product 8 (163.7 mg, 58.9%). $^1$H NMR δ (ppm)($CH_3OH$-$d_4$): 1.19 (3 H, s), 1.60-1.59 (1 H, m), 1.82 (1 H, q, J=10.32 Hz), 2.35-2.30 (4 H, m), 4.17 (1 H, d, J=9.54 Hz), 4.38 (1 H, br s), 4.58 (1 H, br s), 4.70 (1 H, s), 4.86-4.80 (1 H, m), 5.76 (1 H, d, J=8.05 Hz), 6.01 (1 H, s), 7.70 (1H, d, J=8.06 Hz).

Step D: Synthesis of Compound 9

A stirred solution of compound Int-6d (226.8 mg, 0.57 mmol) in MeOH (6 ml), was added Pd/C (10% w/w, 23 mg, 10% wt), affixed a $H_2$ balloon, stirred at room temperature for 1 hour. Filtered the reaction mixture through a Celite plug and washed with MeOH (20 ml). The filtrate was concentrated in vacuo. The residue was purified using silica gel flash column chromatography (0-10% MeOH/$CH_2Cl_2$) to provide the product 9 (112.7 mg, 53.2%). $^1$H NMR δ (ppm)($CH_3OH-d_4$): 1.20 (3 H, s), 1.58-1.55 (1 H, m), 1.81 (1 H, q, J=10.40 Hz), 2.25 (2 H, t, J=10.50 Hz), 2.38 (2 H, d, J=9.29 Hz), 4.36 (1 H, d, J=9.70 Hz), 4.50 (1 H, br s), 4.63 (1 H, br s), 4.72 (1 H, br s), 4.84 (1 H, s), 5.76 (1 H, d, J=8.13 Hz), 6.03 (1 H, s), 7.65 (1 H, d, J=8.12 Hz).

Example 7

Preparation of Compound 10

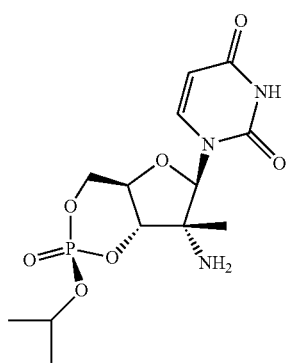

10

Compound 10 was prepared using the methods described in International Publication No. WO 2012/142085.

Example 8

Replicon Activity and Cytotoxicity Assays

To measure cell-based anti-HCV activity of the compounds of the present invention, replicon cells (1b-Con1) are seeded at 5000 cells/well in 96-well plates one day prior to treatment with a compound of the invention. Various concentrations of a test compound of the invention in DMSO are then added to the replicon cells, with the final concentration of DMSO at 0.5% and fetal bovine serum at 10% in the assay media. Cells are harvested three days post-dosing and the replicon RNA level is determined using real-time RT-PCR (Taqman assay) with GAPDH RNA as endogenous control. $EC_{50}$ values are calculated from experiments with 10 serial twofold dilutions of the inhibitor in triplicate. To measure cytotoxicity in replicon cells of an inhibitor, an MTS assay is performed according to the manufacturer's protocol for CellTiter 96 Aqueous One Solution Cell Proliferation Assay (Promega, Cat #G3580) three days post dosing on cells treated identically as in replicon activity assays. $CC_{50}$ is the concentration of inhibitor that yields 50% inhibition compared to vehicle-treated cells. Cytotoxicity in other types of cells can be measured using the same MTS protocol.

Data was obtained using this method for selected compounds of the present invention, and is set forth below. This data indicates that the compound possesses significant cytotoxicity windows over replicon activity.

| Compound | Replicon (1a) $EC_{50}$ (μM) | Cytotoxicity (μM) |
|---|---|---|
| 10 | >100 | >100 |
| 1 | 56.2 | >100 |
| 3 | >100 | >100 |

-continued

| Compound | Replicon (1a) EC$_{50}$ (μM) | Cyto-toxicity (μM) |
|---|---|---|
| 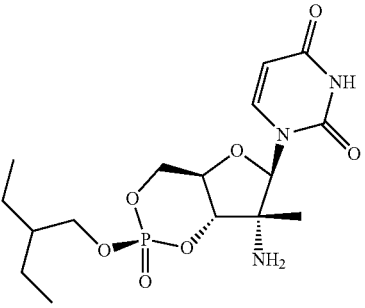 5 | 43.2 | >100 |
| 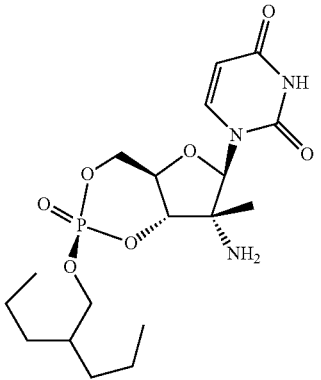 7 | >100 | >100 |
| 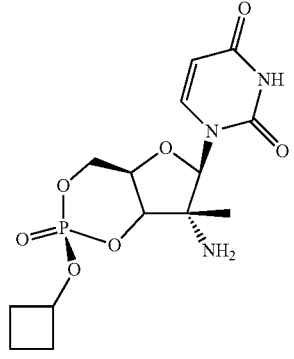 8 | >100 | >100 |

Example 9

In Vitro Conversion of Prodrug to Nucleoside Triphosphate

The degree of conversion of a prodrug compound of the present invention to its corresponding nucleoside triphosphate is measured in vitro using the procedure described below.

A 2 mM stock solution of the prodrug test compound is prepared in 5% DMSO/95% MeOH to provide a final sample concentration of 10 μM. A 5 μL aliquot is removed from this stock solution and added to 1 mL of either a rat or human cryopreserved hepatocyte sample to provide a control sample at a concentration of 1 million cells/mL. This sample is assayed in triplicate and used as a test sample.

A 2 mM stock solution of Compound A is prepared in 5% DMSO/95% MeOH to provide a final sample concentration of 10 μM.

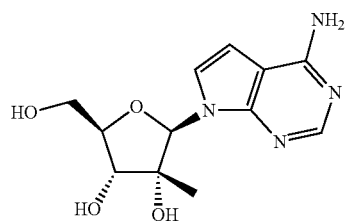 [SMILES: C[C@@]1(O)[C@H](O)[C@@H](CO)O[C@H]1n1ccc2c(N)ncnc21]

Compound A

A 5 μL aliquot is removed from this stock solution and added to 1 mL of either a rat or human cryopreserved hepatocyte sample to provide a control sample at a concentration of 1 million cells/mL. This sample is assayed in triplicate and used as a control standard.

Human and rat hepatocytes are removed from liquid nitrogen storage and thawed by submerging the hepatocyte tube into a pre-heated 37° C. waterbath and gently shaking the tube back & forth until thawed. The thawed hepatocytes are then gently poured into a container of Hepatocyte Basal Medium (50 mL, pre-warmed to 37° C.) and washed. The hepatocyte tube is then rinsed out with pre-warmed Hepatocyte Basal Medium and the washed hepatocytes and rinse are combined and centrifuged at 500 rpm for 4 minutes at room temperature. The supernatant is then discarded and the resulting hepatocyte pellet is resuspended with Hepatocyte Basal Medium (pre-warmed to 37° C.) and the final hepatocyte concentration is adjusted to 1 million cells/mL to provide the final hepatocyte suspension.

A 1 mL aliquot is removed from the 1 million cells/mL final hepatocyte suspension, analyzed in triplicate and placed into 20 mL scintillation vial without a cap. 2 mM of the prodrug test sample is then added into the hepatocyte suspension to provide a 10 μM final concentration in the 1 mL hepatocyte sample. The sample is then incubated at 37° C./5% CO$_2$ for 4 hours. A blank hepatocyte sample as well as the control standard are also incubated in this fashion.

The incubated hepatocyte suspension samples are transferred to a micro-centrifuge tube using a transfer pipette and centrifuged at 500 rpm for 4 minutes at room temperature. The supernatant is discarded and the resulting hepatocyte pellet was resuspended and the cells are extracted with 0.25 mL of a 4° C. solution of 70% methanol/30%(20 mM EDTA/20 mM EGTA) that has been adjusted to pH 8 using sodium hydroxide. The resulting extract solution is then stored in a refrigerator at 4° C. until ready for use, at which point the sample is first subjected to vortexing/sonication to ensure that all hepatocyte cells have burst. The sample is then centrifuged at 4000 rpm for 10 minutes at 4° C. and a 100 μL aliquot of the resulting supernatant is added into a bioanalytical plate (2 mL Square 96 well plate w/100 uL Tapered Reservoir), with the remaining supernatant immediately stored at −80° C. for re-assay if necessary. The blank control supernatant is transferred to a new tube for use as a control matrix in standard curves.

Alternatively, cryopreserved plateable hepatocytes are obtained from Celsis-In Vitro Technologies (Baltimore, Md.), and plated according to manufacturer's protocol at 0.7×10⁶ cells/mL in InVitro GRO CP Medium (1.75×10⁶ cells/well in 6-well plates) three hours prior to inhibitor treatment. An inhibitor in DMSO at the indicated concentration in InVitro GRO CP Medium is added to the hepatocytes at t=0. At indicated times up to 48 hours post dosing, cells are washed in ice-cold PBS, extracted with ice-cold 1 mL 70% methanol: 30% 20 mM EDTA/EGTA and centrifuged. The supernatant is stored at −80° C. until analysis. For intracellular NTP analysis, an NTP calibration curve is first generated by spiking a blank extraction buffer with known concentrations of the NTP standard. LC/ESI-MS analysis is performed on a QTRAP 5500 LC/MS/MS system (Applied Biosystems, Foster City, Calif.) coupled to a Shimazu UFLC system, operated in the positive-ion mode. The HPLC system is consisted of solvent delivery module (LC20-AD XR), auto injector (SIL-20ACXR), and photodiode array detector (SPD-M20A PDA) (Shimadzu Corporation, Tokyo, Japan). All HPLC separations are performed at 40° C. The test samples are analyzed on a BioBasic AX column (5 μm particle size, 100×2.1 mm I.D., Thermo Scientific) using A (Acetonitrile:10 mM NH₄Ac=30:70, v:v, pH=6) and B (Acetonitrile:1 mM NH₄Ac=30:70, v:v, pH=10) as mobile phases at a flow rate of 1.0 mL/min. The injection volume is 50 μL. The mobile phase gradient starts at 0% B, and linearly increases to 100% B over 6 min. The MS analysis of all NTPs is performed on the same QTRAP 5500 MS instrument in the multiple ion monitoring mode (MRM), with Turbo-Ion-Spray ionization. The collision energy is 40 eV for all the analytes and standards. The quadrupole mass analyzer is set to unit resolution.

Results are reported in pmol of triphosphate per μL of cells. To estimate μM intracellular concentration of nucleoside triphosphate, the following conversion is applied: 1×10⁶ hepatocytes is 3 μL in volume.

| Compound | Intracellular NTP in Human Hepatocyte (uM) |
|---|---|
| 10 | 146 |
| 1 | 3323 |
| 3 | 651 |
| 5 | 11166 |

| Compound | Intracellular NTP in Human Hepatocyte (uM) |
|---|---|
| 7 (structure) | 1081 |
| 8 (structure) | 171 |

Example 10

Determination of In Vivo Conversion of Prodrug to Nucleoside Triphosphate

The degree of conversion of a prodrug compound of the present invention to its corresponding nucleoside triphosphate is measured in vivo using the procedure described below.

Liver samples are collected from either Wistar Hannover Rats or Beagle Dogs dosed with the prodrug via the freeze clamp procedure (animals anesthetized via isofluorane, the liver is clamped with modified clamps that are frozen in liquid nitrogen, and then the clamped liver piece is placed in liquid nitrogen to ensure frozen completely; repeat liver clamp procedure to get a second piece of liver sample; samples stored at −80° C.). Liver samples are homogenized using a a Spex Sample Prep Freezer/Mill (Cryomill); settings for the cryomill operation are 1 Cycle, 2 minute pre-chill time, 2 minute run time, 1 minute cool time, and a rate of 15 cycles/second (cps). Control liver samples collected from rats dosed with vehicle are cryomilled in the same manner. During this process it is imperative that anything that will come into contact with the liver samples remain frozen on dry ice at all times, such as all Cryomill sample containers/lids and spatulas.

The cryomilled control liver sample is used to generate the standard curve. Weigh out an appropriate amount of cryomilled control liver sample into a conical tube, depending on how many standard curves are needed, place on wet ice and suspend with cold (approx. 0° C.) 70% Methanol/30% (20 mM EDTA/EGTA) that had been adjusted to pH 8 with sodium hydroxide at a ratio of 1:4 (liver:MeOH/EDTA-EGTA). The suspended liver homogenate is vortexed until a homogenous suspension is obtained. The standard curve ranges from 10 ng/mL to 50,000 ng/mL of NTP standard, as well as a QC sample at 10,000 ng/mL. A 500 µL aliquot of suspended control liver homogenate per each point on the standard curve and each QC is removed and placed into a 1.5 mL centrifuge tube, and 125 µL of each corresponding standard curve or QC standard solution is added to each individual control aliquot and re-vortexed. Liver sample aliquots are centrifuged at 4° C., 3645×g, for 10 minutes, and 450 µL of the supernatant is aliquoted into a 2 mL Square 96 well bioanalytical plate. Single and double blank samples are also generated from the suspended control liver homogenate using the procedure above, substituting the 125 µL of standard solution with 125 µL of water.

Approximately 1-2 grams of the cryomilled liver sample is weighed out into a 50 mL conical tube and placed on wet ice and suspended with cold 70% Methanol/30% (20 mM EDTA/EGTA) that had been adjusted to pH 8 with sodium hydroxide at a ratio of 1:4 (liver:MeOH/EDTA-EGTA); the remaining cryomilled liver sample is stored at −80° C. for possible re-assay if needed. The suspended liver homogenate is vortexed until a homogenous suspension is obtained. A 500 µL aliquot of each unknown liver sample is removed and placed into a 1.5 mL centrifuge tube, and 125 µL of water is added to each aliquot and re-vortexed. Standard curve/QC liver sample aliquots are centrifuged at 4° C., 3645×g, for 10 minutes, and 450 µL of the supernatant is aliquoted into a 2 mL square 96 well bioanalytical plate, and an appropriate internal standard is added to all sample wells, standard curve/QC wells, and the single blank well. The sample plate is stored at −80° C. until analysis and results are reported in µM of NTP measured.

| Compound | Dog Liver NTP Concentration at 4 h (uM) | Dose (mpk) |
|---|---|---|
| 10 (structure) | 1 | 10 |

-continued

| Compound | Dog Liver NTP Concentration at 4 h (uM) | Dose (mpk) |
|---|---|---|
| 1 | 8.8 | 4.5 |
| 3 | 2.6 | 10 |
| 5 | 3 | 5 |

-continued

| Compound | Dog Liver NTP Concentration at 4 h (uM) | Dose (mpk) |
|---|---|---|
| 7 | NA | NA |
| 8 | NA | NA |

NA = not available

The present invention is not to be limited by the specific embodiments disclosed in the examples that are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

A number of references have been cited herein, the entire disclosures of which are incorporated herein by reference.

What is claimed is:

1. A compound having the formula (I):

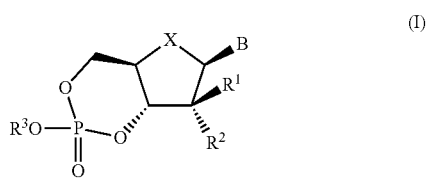

or a pharmaceutically acceptable salt thereof, wherein:

B is:

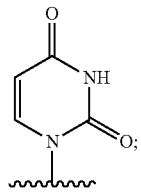

X is O, N(H), S or CH$_2$;

R$^1$ is H, C$_1$-C$_3$ alkyl, C$_2$-C$_3$ alkenyl or C$_2$-C$_3$ alkynyl;

R$^2$ is —N(R$^6$)$_2$;

R$^3$ is H, C$_6$-C$_{20}$ alkyl, —(C$_1$-C$_3$ alkylene)$_m$-(C$_3$-C$_7$ cycloalkyl) or —(C$_1$-C$_3$ alkylene)$_m$-(C$_6$-C$_{10}$ aryl); wherein said C$_6$-C$_{20}$ alkyl group, said C$_3$-C$_7$ cycloalkyl group and said C$_6$-C$_{10}$ aryl group can be optionally substituted with up to five groups, each independently selected from C$_1$-C$_6$ alkyl, C$_2$-C$_6$ alkenyl, C$_2$-C$_6$ alkynyl, C$_3$-C$_7$ cycloalkyl, C$_6$-C$_{10}$ aryl, 5- or 6-membered monocyclic heteroaryl, 9- or 10-membered bicyclic heteroaryl, halo, —OR$^7$, —SR$^7$, —S(O)R$^7$, —S(O)$_2$R$^7$, —S(O)$_2$N(R$^7$)$_2$, C$_1$-C$_6$ haloalkyl, C$_1$-C$_6$ hydroxyalkyl, —O—(C$_1$-C$_6$ haloalkyl), —CN, —NO$_2$, —N(R$^7$)$_2$, —C(O)OR$^7$, —C(O)N(R$^7$)$_2$ and —NHC(O)R$^7$, —NHC(O)OR$^7$ and —NHC(O)N(R$^7$)$_2$;

each occurrence of R$^4$ is independently H, C$_1$-C$_6$ alkyl, C$_1$-C$_6$ haloalkyl, C$_1$-C$_6$ hydroxyalkyl, —(C$_1$-C$_3$ alkylene)$_m$-(C$_3$-C$_7$ cycloalkyl), —(C$_1$-C$_3$ alkylene)$_m$-(C$_6$-C$_{10}$ aryl), —(C$_1$-C$_3$ alkylene)$_m$-(4 to 7-membered heterocycloalkyl), —(C$_1$-C$_3$ alkylene)$_m$-(5- or 6-membered monocyclic heteroaryl) or —(C$_1$-C$_3$ alkylene)$_m$-(9- or 10-membered bicyclic heteroaryl);

R$^5$ is H or —C(O)—(C$_1$-C$_{20}$ alkyl);

each occurrence of R$^6$ is independently H, C$_1$-C$_6$ alkyl, C$_3$-C$_7$ cycloalkyl, phenyl or benzyl;

each occurrence of R$^7$ is independently H, C$_1$-C$_{10}$ alkyl, C$_1$-C$_6$ haloalkyl, C$_1$-C$_6$ hydroxyalkyl, —(C$_1$-C$_3$ alkylene)$_m$-(C$_3$-C$_7$ cycloalkyl), —(C$_1$-C$_3$ alkylene)$_m$-(C$_6$-C$_{10}$ aryl), —(C$_1$-C$_3$ alkylene)$_m$-(4 to 7-membered heterocycloalkyl), —(C$_1$-C$_3$ alkylene)$_m$-(5- or 6-membered monocyclic heteroaryl) or —(C$_1$-C$_3$ alkylene)$_m$-(9- or 10-membered bicyclic heteroaryl), wherein said C$_3$-C$_7$ cycloalkyl group, said C$_6$-C$_{10}$ aryl group, said 4 to 7-membered heterocycloalkyl group, said -5- or 6-membered monocyclic heteroaryl group or said 9- or 10-membered bicyclic heteroaryl group can be optionally substituted with R$^8$;

R$^8$ represents from one to five substituent groups, each independently selected from C$_1$-C$_6$ alkyl, C$_2$-C$_6$ alkenyl, C$_2$-C$_6$ alkynyl, halo, —OR$^4$, —SR$^4$, C$_1$-C$_6$ haloalkyl, C$_1$-C$_6$ hydroxyalkyl, —O—(C$_1$-C$_6$ haloalkyl), —CN, —NO$_2$, —N(R$^4$)$_2$, —C(O)OR$^4$, —C(O)N(R$^4$)$_2$ and —NHC(O)R$^4$; and each occurrence of m is independently 0 or 1.

2. The compound of claim 1, wherein X is O.

3. The compound of claim 1, wherein R$^1$ is methyl.

4. The compound of claim 1, wherein R$^2$ is —NH$_2$.

5. The compound of claim 1, wherein R$^3$ is C$_6$-C$_{20}$ alkyl, —(C$_1$-C$_3$ alkylene)$_m$-(C$_6$-C$_{10}$ aryl) or C$_3$-C$_7$ cycloalkyl.

6. The compound of claim 5, wherein R$^3$ is cyclobutyl, cyclopentyl, benzyl, —CH$_2$CH(CH$_2$CH$_2$CH$_3$)$_2$ or —CH$_2$CH(CH$_2$CH$_3$)$_2$.

7. The compound of claim 1 having the structure:

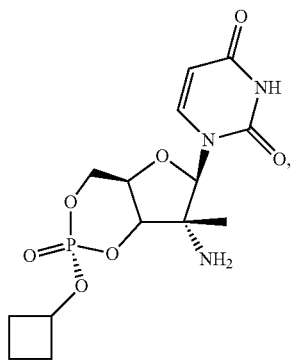

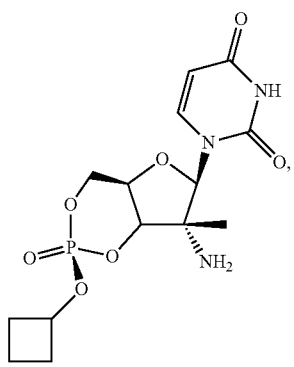

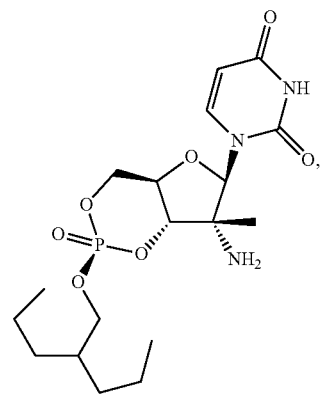

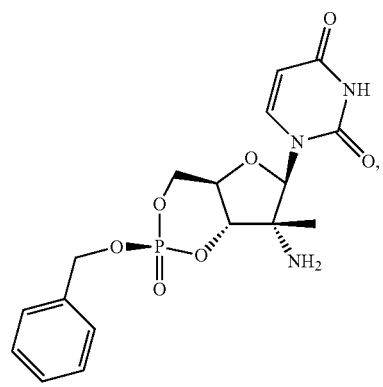

-continued

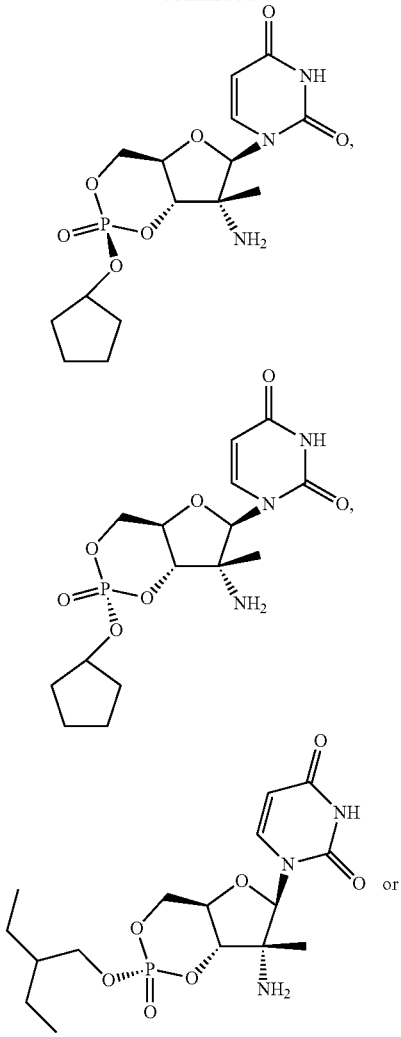

-continued

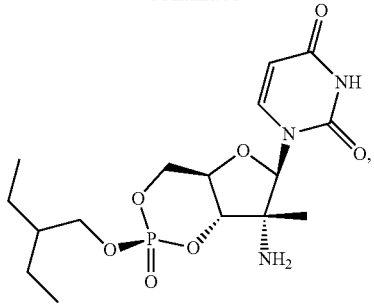

or a pharmaceutically acceptable salt thereof.

8. A pharmaceutical composition comprising an effective amount of the compound of claim 1, or a pharmaceutically acceptable salt thereof, and a pharmaceutically acceptable carrier.

9. The pharmaceutical composition according to claim 8, further comprising a second therapeutic agent selected from the group consisting of HCV antiviral agents, immunomodulators, and anti-infective agents.

10. The pharmaceutical composition according to claim 9, further comprising a third therapeutic agent selected from the group consisting of HCV protease inhibitors, HCV NS5A inhibitors and HCV NS5B polymerase inhibitors.

11. A method of treating a patient infected with HCV comprising the step of administering an amount of the compound according to claim 1, or a pharmaceutically acceptable salt thereof, effective to prevent and/or treat infection by HCV in said patient.

12. The method according to claim 11, further comprising the step of administering to said patient a second therapeutic agent selected from the group consisting of HCV antiviral agents, immunomodulators, and anti-infective agents.

13. The method according to claim 12, further comprising the step of further comprising the step of administering to said patient a third therapeutic agent selected from the group consisting of HCV protease inhibitors, HCV NS5A inhibitors and HCV NS5B polymerase inhibitors.

* * * * *